| (12) | United States Patent | (10) Patent No.: | US 7,630,078 B1 |
|---|---|---|---|
| | Nabutovsky et al. | (45) Date of Patent: | Dec. 8, 2009 |

(54) CALIBRATING IMPLANTABLE OPTICAL SENSORS

(75) Inventors: Yelena Nabutovsky, Mountain View, CA (US); Gene A. Bornzin, Simi Valley, CA (US); Taraneh Ghaffari Farazi, San Jose, CA (US); John W. Poore, South Pasadena, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 368 days.

(21) Appl. No.: 11/683,521

(22) Filed: Mar. 8, 2007

Related U.S. Application Data

(63) Continuation-in-part of application No. 11/282,198, filed on Nov. 17, 2005, which is a continuation of application No. 11/231,555, filed on Sep. 20, 2005.

(51) Int. Cl.
   *G01B 9/08* (2006.01)
(52) U.S. Cl. .................................. 356/392; 356/394
(58) Field of Classification Search ............. 356/36–39, 356/392–394
   See application file for complete search history.

(56) References Cited

U.S. PATENT DOCUMENTS

| 3,847,483 | A | 11/1974 | Shaw et al. |
|---|---|---|---|
| 4,114,604 | A | 9/1978 | Shaw et al. |
| 4,686,988 | A | 8/1987 | Sholder |
| 4,708,142 | A | 11/1987 | DeCote, Jr. |
| 4,712,555 | A | 12/1987 | Thornander et al. |
| 4,729,376 | A | 3/1988 | DeCote, Jr. |
| 4,788,980 | A | 12/1988 | Mann et al. |
| 4,809,697 | A | 3/1989 | Causey, III et al. |
| 4,815,469 | A | 3/1989 | Cohen |
| 4,940,052 | A | 7/1990 | Mann et al. |
| 4,944,298 | A | 7/1990 | Sholder |
| 4,944,299 | A | 7/1990 | Silvian |
| 4,969,467 | A | 11/1990 | Callaghan et al. |
| 5,350,410 | A | 9/1994 | Kleks et al. |
| 5,494,032 | A | * | 2/1996 | Robinson et al. ............ 600/323 |
| 5,553,615 | A | 9/1996 | Carim et al. |
| 5,608,207 | A | 3/1997 | Allen |

(Continued)

OTHER PUBLICATIONS

Bornzin et al., "Measuring Oxygen Saturation and Hematocrit Using a Fiberoptic Catheter", IEEE/9th Annual Conf. of the Eng. & Biol. Soc., 1997.

(Continued)

*Primary Examiner*—Michael P Stafira
(74) *Attorney, Agent, or Firm*—Steven M. Mitchell

(57) ABSTRACT

A measurement light detector detects light transmitted by a light source of an implantable system that is scattered back into an implantable housing, and produces a measurement signal indicative of the intensity of the light detected by the measurement light detector. A calibration light detector detects a portion of the transmitted light that has not exited the housing, and produces a calibration signal that is indicative of the intensity of the light detected by the calibration light detector, which is indicative of the intensity of the light transmitted by the light source. Changes in the intensity of the transmitted light are compensated for based on the calibration signal produced by the calibration light detector. This description is not intended to be a complete description of, or limit the scope of, the invention. Other features, aspects, and objects of the invention can be obtained from a review of the specification, the figures, and the claims.

17 Claims, 17 Drawing Sheets

U.S. PATENT DOCUMENTS

| | | |
|---|---|---|
| 6,275,734 B1 | 8/2001 | McClure et al. |
| 6,289,229 B1 | 9/2001 | Crowley |
| 6,491,639 B1 | 12/2002 | Turcott |
| 6,526,298 B1 | 2/2003 | Khalil |
| 6,561,984 B1 | 5/2003 | Turcott |
| 6,567,678 B1 | 5/2003 | Oosta |
| 6,662,031 B1 | 12/2003 | Khalil |
| 6,731,967 B1 | 5/2004 | Turcott |
| 7,146,203 B2 | 12/2006 | Botvinick |
| 7,230,222 B2 | 6/2007 | Cheng |
| 2002/0026106 A1 | 2/2002 | Khalil |
| 2005/0027178 A1 | 2/2005 | Iddan |
| 2007/0060811 A1 | 3/2007 | Roberts |

OTHER PUBLICATIONS

Non-Final Office Action mailed Mar. 25, 2009: Related U.S. Appl. No. 11/282,198.

Non-Final Office Action mailed Apr. 15, 2009: Related U.S. Appl. No. 11/231,555.

\* cited by examiner

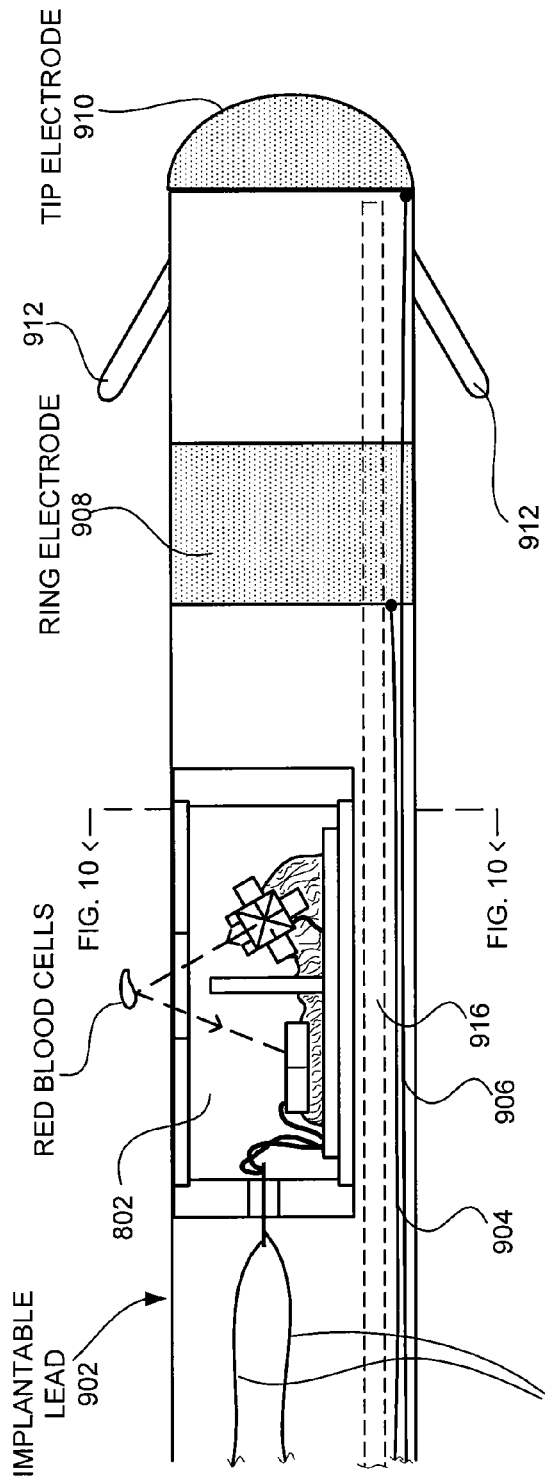
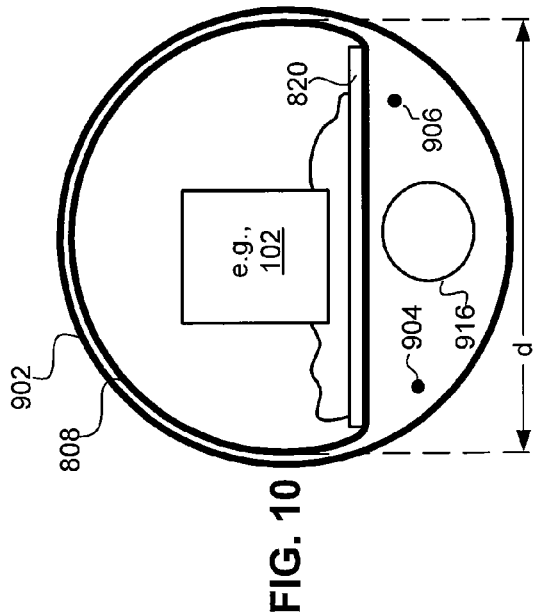
FIG. 9
FIG. 10

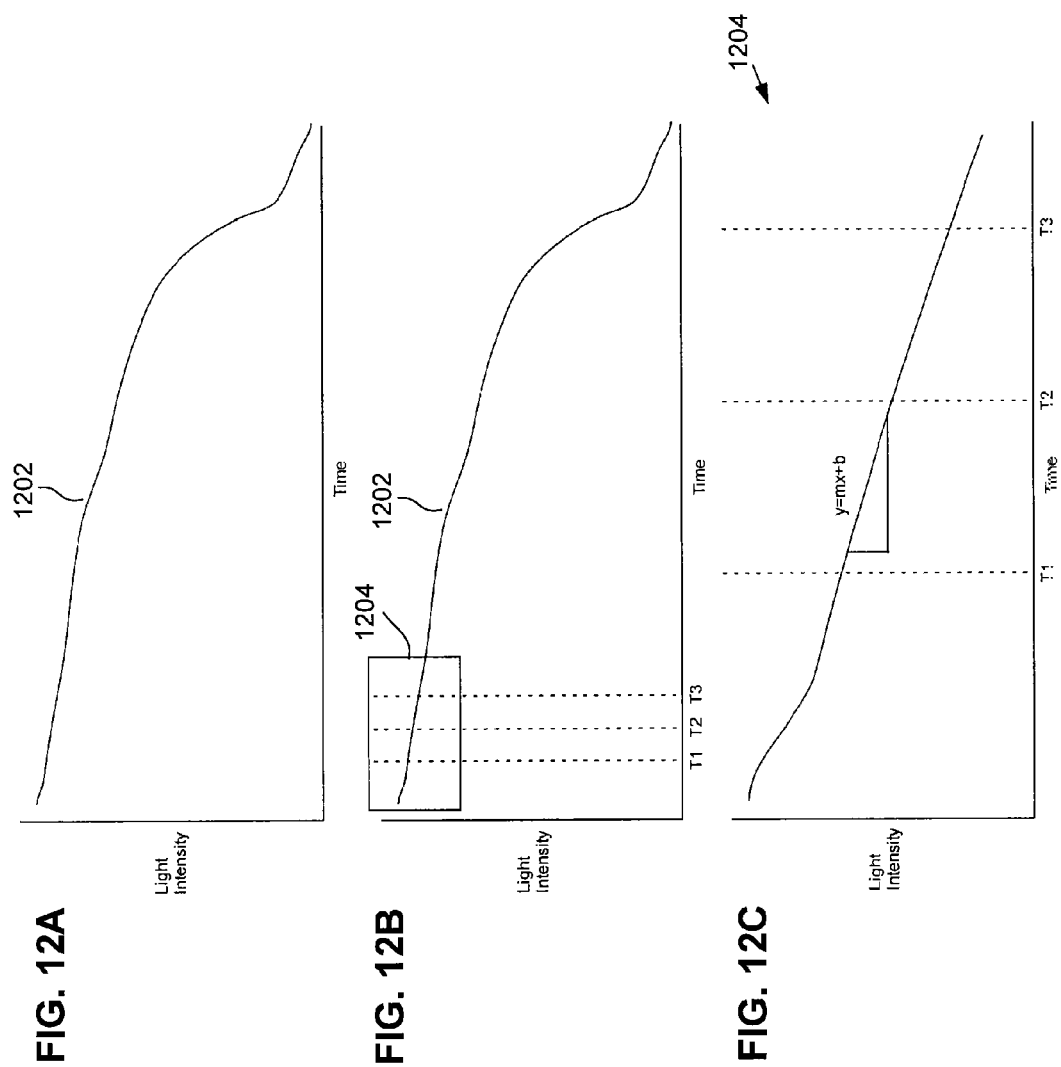

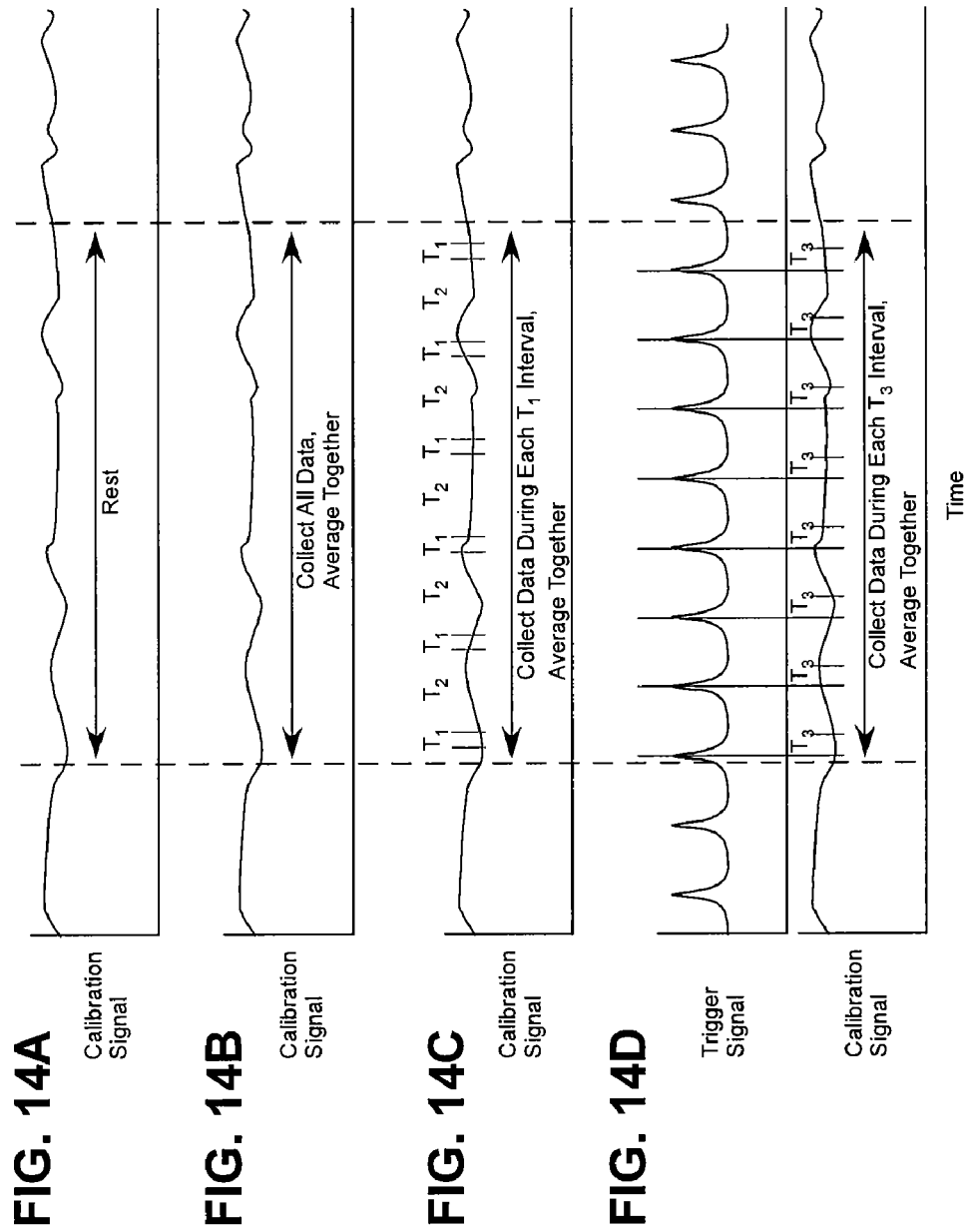

CALIBRATING IMPLANTABLE OPTICAL SENSORS

PRIORITY CLAIM

The present application is a continuation-in-part of U.S. patent application Ser. No. 11/282,198, entitled "Implantable Self-Calibrating Optical Sensors", filed Nov. 17, 2005, by John W. Poore, which is incorporated herein by reference. The present application is also a continuation-in-part of U.S. patent application Ser. No. 11/231,555, entitled "Implantable Multi-Wavelength Oximeter Sensor," filed Sep. 20, 2005, by John W. Poore, which is incorporated herein by reference.

FIELD OF THE INVENTION

Embodiments of the present invention relate to implantable optical sensors, and methods for use therewith, that are used, e.g., for obtaining measures of blood oxygen saturation and/or hematocrit. Embodiments of the present invention also relate to taking calibration measurements and performing calibrations to compensate for changes in the intensity of light transmitted by light sources of implantable optical sensors.

BACKGROUND

Blood oxygen saturation is the relative amount of oxygenated hemoglobin in all of the hemoglobin present in the blood stream. This hemoglobin is packaged in biconcave discs of approximately 10 micrometers diameter which commonly occur with a density of approximately five million red blood cells per cubic millimeter. When radiant energy (e.g., light) is incident upon red blood cells, the red blood cells both scatter and transmit the incident radiant energy. The differential absorption by oxygenated and non-oxygenated hemoglobin of the radiant energy reflected by and transmitted through the red blood cells furnishes the basis for the oxygen saturation measurements.

More specifically, pulse oximeters use light of two or more different centered wavelengths (e.g., produced by two or more light sources) to obtain measures of blood oxygen saturation by measuring the absorption and/or scattering of oxyhemoglobin and reduced hemoglobin. The measured scattering data allows for the calculation of the relative concentrations of reduced hemoglobin and oxyhemoglobin, and therefore blood oxygen saturation levels, since the scattering relationships are known.

Most multi-wavelength pulse oximeters are non-implantable devices that are clipped onto a patients finger or ear lobe. However, it is believed that it would be beneficial to chronically implant pulse oximeters so that measures of oxygen saturation and hematocrit (the density of red blood cells) can be used as feedback for pacing optimization, disease monitoring, and the like.

Some multi-wavelength implantable oximeter catheters are known, as can be appreciated from U.S. Pat. Nos. 3,847, 483 and 4,114,604, each of which are incorporated herein by reference. For multi-wavelength oximeters to work properly, light from two or more light sources (e.g., from 670, 700 and 805 nm wavelength LEDs) should be combined into a single beam, to assure that the computed oxygen saturation is accurate with varying blood flow rate, pH, hematocrit and hemoglobin. In the devices of the '483 and '604 patents, fiber optic guides are used to combine the light of multiple wavelengths into the single beam. This, however, requires significant physical space. Thus, in the devices of the '482 and '604 patents, the light sources and fiber optic guides are located in a housing that is a distance from the measurement site, and optical fibers that are within a catheter are used to deliver the combined light beam to the measurement site at the distal end of the catheter.

It would be beneficial if an implantable optical combiner requiring less physical space can be provided, thereby enabling the optical combiner to be located at the measurement site.

The light sources that are used to produce the light useful for obtaining measures of blood oxygen saturation, etc., may produce light of less intensity as such light sources age. If not compensated for, this will effect the intensity of the scattered light detected by a photo detector, which will in turn adversely effect determinations of blood oxygen saturation, etc. Accordingly, there is also a need to compensate for changes in the intensity of the light produced by such light sources.

SUMMARY

Embodiments of the present invention are directed to implantable systems, and methods for use therewith, that compensate for changes in the intensity of light transmitted by one or more light sources of the implantable systems. Such changes in intensity can be due, e.g., to aging of the light sources. The light sources can be, e.g., light emitting diodes (LEDs), but are not limited thereto.

In accordance with specific embodiments of the present invention, the implantable system includes an implantable housing including a window through which light can pass. The term window, as used herein, is intended to collectively encompass all portions of the housing through which light of interest can enter and exit the housing, even if such portions are separated from one another (e.g., by opaque portions). Included within the housing is at least one light source, a measurement light detector and a calibration light detector. Each light source transmits light of a corresponding wavelength. The intensity of the light transmitted by each light source is controlled by a corresponding drive signal that drives the light source. A portion of the light of each wavelength exits the housing through the window. The measurement light detector detects light of each wavelength scattered back into the housing through the window, and produces a measurement signal that is indicative of the intensity of the light of each wavelength detected by the measurement light detector. The calibration light detector detects a portion of the light of each wavelength that has not exited the housing, to produce a calibration signal that is indicative of the intensity of the light of the wavelength detected by the calibration light detector, which is indicative of the intensity of the light transmitted by each light source.

In accordance with specific embodiments, a controller adjusts each drive signal, based on the calibration signal, to keep the intensity of the light transmitted by each light source substantially constant. In accordance with other embodiments of the present invention, a controller adjusts the measurement signal, based on the calibration signal, to compensate for changes in the intensity of the light transmitted by each light source. In still other embodiments, rather than adjusting signals, a processor (that uses the measurement signal for a diagnostic and/or therapeutic purpose) detects changes in the intensity of the light transmitted by each light source based on the calibration signal, and takes into account the changes in intensity when using the measurement signal for a diagnostic and/or therapeutic purpose. For example, the processor can take such changes in intensity into account by making appropriate adjustments to algorithms that are used to determine levels of blood oxygen saturation and/or levels hematocrit based on the measurement signal.

In specific embodiments, calibration measurements are produced based on the calibration signal, and the calibration measurements are used to perform calibrations that compensate for changes in the intensity of light transmitted by the light source. In certain embodiments, the calibrations measurements are produced less frequently than calibrations are performed, to conserve power and processing resources. For example, between consecutive calibration measurements, a metric indicative of a change in the intensity of the light since a most recent calibration measurement is predicted, and the predicted metric is used to perform a calibration that compensates for predicted depletion in the intensity of light transmitted by the light source. In specific embodiments, a depletion curve can be estimated for the light source based on calibration measurements, or if available, the depletion curve can be obtained from light source manufacturer. Between consecutive calibration measurements, the estimated depletion curve can be used to perform a calibration that compensates for predicted depletion in the intensity of light transmitted by the light source.

This summary is not intended to be a complete description of the invention. Other features, aspects, objects and advantages of the invention can be obtained from a review of the specification, the figures, and the claims.

BRIEF DESCRIPTION OF THE DRAWINGS

FIG. 9 illustrates an implantable lead that includes the sensor of FIG. 8A, in accordance with an embodiment of the present invention.

FIG. 10 illustrates a rough cross-section of the lead shown in FIG. 9.

FIG. 12A illustrates a depletion curve for an exemplary LED type light source.

FIG. 12B is used to illustrate how calibration measurements can be used to identify points along a depletion curve.

FIG. 12C, which is a zoomed in view of a portion of the curve shown in FIG. 12B, is used to explain how an equation can be estimated for a depletion curve.

FIG. 14A illustrates an exemplary portion of a calibration signal, which includes a an exemplary rest period.

FIG. 14B is used to explain how data collected from the rest period shown in FIG. 14A can be combined to produce a calibration measurement, in accordance with specific embodiments of the present invention.

FIG. 14C is used to explain that data need not be continually collected during a rest period, to produce a calibration measurement.

FIG. 14D illustrates how features of an EGM can be used as triggers for collecting calibration data used to produce a calibration measurement.

DETAILED DESCRIPTION

Figure 1:
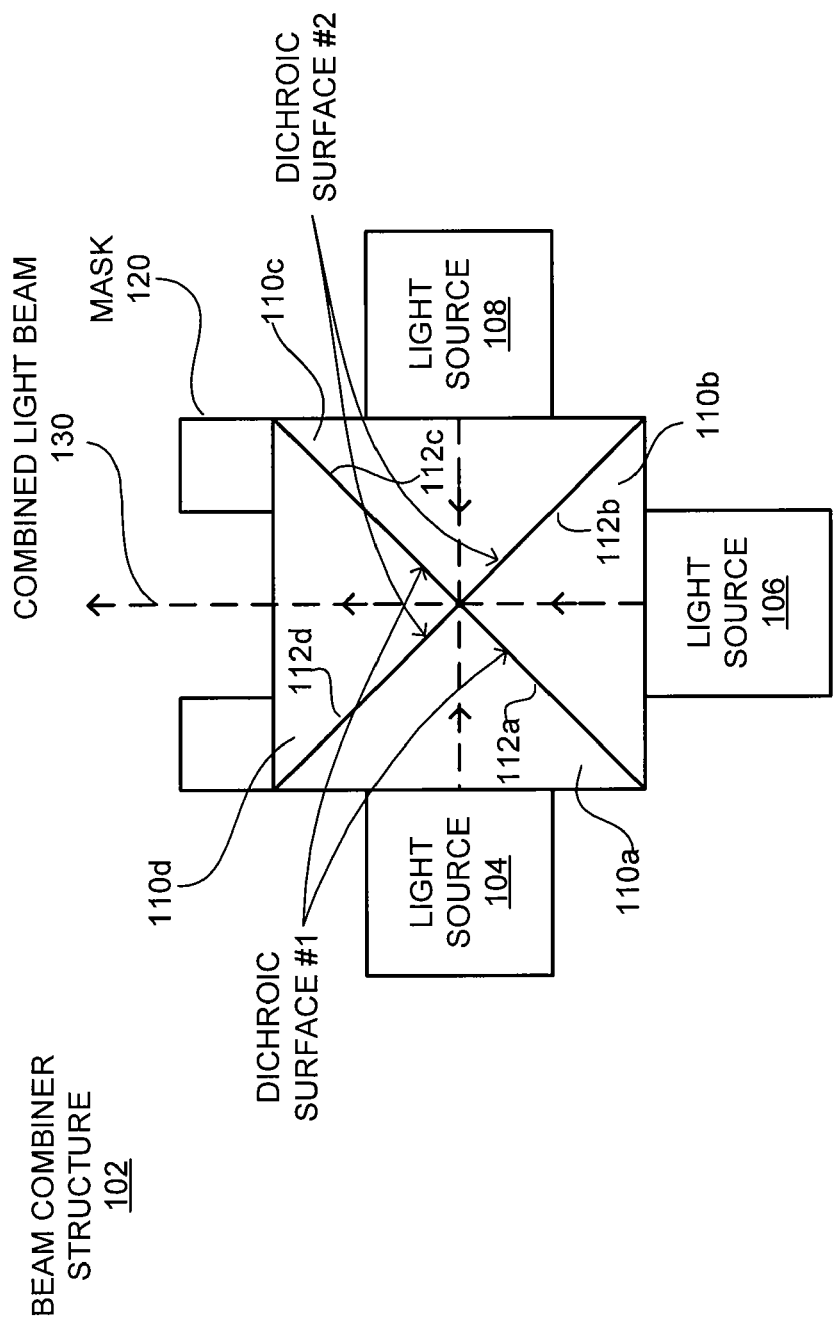
FIG. 1 illustrates an apparatus for combining light of three different wavelengths from three physically separate light sources, according to an embodiment of the present invention.

The following description is of the best modes presently contemplated for practicing various embodiments of the present invention. This description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. Also, the left-most digit(s) of a reference number identifies the drawing in which the reference number first appears.

FIG. 1 shows a first embodiment of the present invention that combines light of three different wavelengths from three physically separate miniature light sources using dichroic surfaces. Such dichroic surfaces are likely dichroic mirrors, but can be dichroic filters, or combinations thereof. Dichroic surfaces have the property of reflecting light of specific wavelengths and passing light of other wavelengths.

Referring to FIG. 1, a beam combiner structure 102, in accordance with an embodiment of the present invention, includes three physically separate light sources 104, 106 and 108, each of which produces radiation of a different wavelength (e.g., 670, 700 and 805 nm). The light sources are preferably light emitting diodes (LEDs), but can be other less preferable sources such as, but not limited to, laser diodes and incandescent lamps. The light sources are shown as being mounted to a structure (a cube in this example) which is made up of four triangular prisms 110a, 110b, 110c and 110d that are bonded together, e.g., using an optical cement or some other clear epoxy resin. Appropriate sides of the prisms are coated to thereby form a pair of dichroic surfaces, labeled dichroic surface #1 and dichroic surface #2. There are multiple ways this can be accomplished. However, it is believed that the most cost effective way is to have only one side of each prism 110a, 110b, 110c and 110d have a dichroic coating. For example, side 112*a* of prism 110*a* and side 112*c* of prism 110*c* can be coated to form dichroic surface #1, and side 112*b* of prism 110*b* and side 112*d* of prism 110*d* can be coated to form dichroic surface #2. While the prisms are likely made of glass, other suitable materials may be used, such as, but not limited to, plastics.

In accordance with an embodiment of the present invention, the dichroic surface #1 will reflect the wavelength ($\lambda_1$) generated by the light source 104, and pass the wavelengths ($\lambda_2$ and $\lambda_3$) generated by light sources 106 and 108. Similarly, the dichroic surface #2 will reflect the wavelength ($\lambda_3$) generated by the light source 108, and pass the wavelengths ($\lambda_1$ and $\lambda_2$) generated by light sources 104 and 106. This can be explained in more detail using an example where the wavelength generated by light source 104 is 670 nm, the wavelength generated by light source 106 is 700 nm, and the wavelength generated by light source 108 is 805 nm (e.g., $\lambda_1$, $\lambda_2$ and $\lambda_3$ are, respectively, 670 nm, 700 nm and 805 nm). Continuing with this example, the present invention can be implemented if dichroic surface #1 reflects light below 685 nm and passes light above 685 nm, and dichroic surface #2 reflects light above 750 nm and passes light below 750 nm.

Still referring to FIG. 1, the dichroic surface #1 and the dichroic surface #2 and the light sources 104 and 108 are positioned (including angled) relative to one another such that light transmitted by the light source 104 is reflected by the dichroic surface #1 to travel in generally a same direction as light transmitted by the light source 108 that is reflected by the dichroic surface #2, as can be appreciated from the dashed lines shown. Additionally, the light source 106 is positioned such that its light, which passes through the dichroic surfaces #1 and #2, travels in generally the same direction as the just mentioned reflected light, as can also be appreciated from the dashed lines shown.

In practice, the light sources 104, 106 and 108 are serially energized, in a non-overlapping temporal relationship. In the manner just described, the light of wavelengths $\lambda_1$, $\lambda_2$ and $\lambda_3$ are combined into a single combined beam 130 that is transmitted toward patient tissue that includes red blood cells. The light of different wavelengths ($\lambda_1$, $\lambda_2$, and $\lambda_3$) are combined into the single beam so that the light of each wavelength shines equally on nearby red blood cells, to thereby increase the likelihood that the computed oxygen saturation is accurate with varying blood flow rate, pH, hematocrit and hemoglobin. A mask 120 may be used to reduce internal reflections.

When transmitted toward patient tissue, some of the light energy is scattered by blood. The different wavelengths are differently scattered, depending on the oxygen saturation level of the blood. After being scattered by blood, the interleaved light stream is received by a light detector (discussed below in more detail with reference to FIG. 8), which preferably produces a separate signal for each of the wavelengths. At a high level, time multiplexing is used to produce a signal path for each of the different wavelengths ($\lambda_1$, $\lambda_2$ and $\lambda_3$) of received light. Each signal path will typically include one or more filters and an A/D converter to sample the received light signals. Using electronic circuitry, firmware and/or software, the received light signals can be analyzed so that oxygen saturation levels can be determined in any well known manner, or in any manner devised in the future.

While three-wavelength pulse oximetry provides more accuracy than two-wavelength pulse oximetry, the accuracy obtained using two-wavelength pulse oximetry is satisfactory for many applications. Accordingly, in accordance with embodiments of the present invention, one of the light sources 104, 106 and 108 can be eliminated. If light source 106 is eliminated, then two dichroic surfaces are still needed, as can be appreciated from FIG. 3. However, if light source 104 (or light source 108) is eliminated, then only a single dichroic surface is necessary, as shown in FIG. 2.

Figure 2:
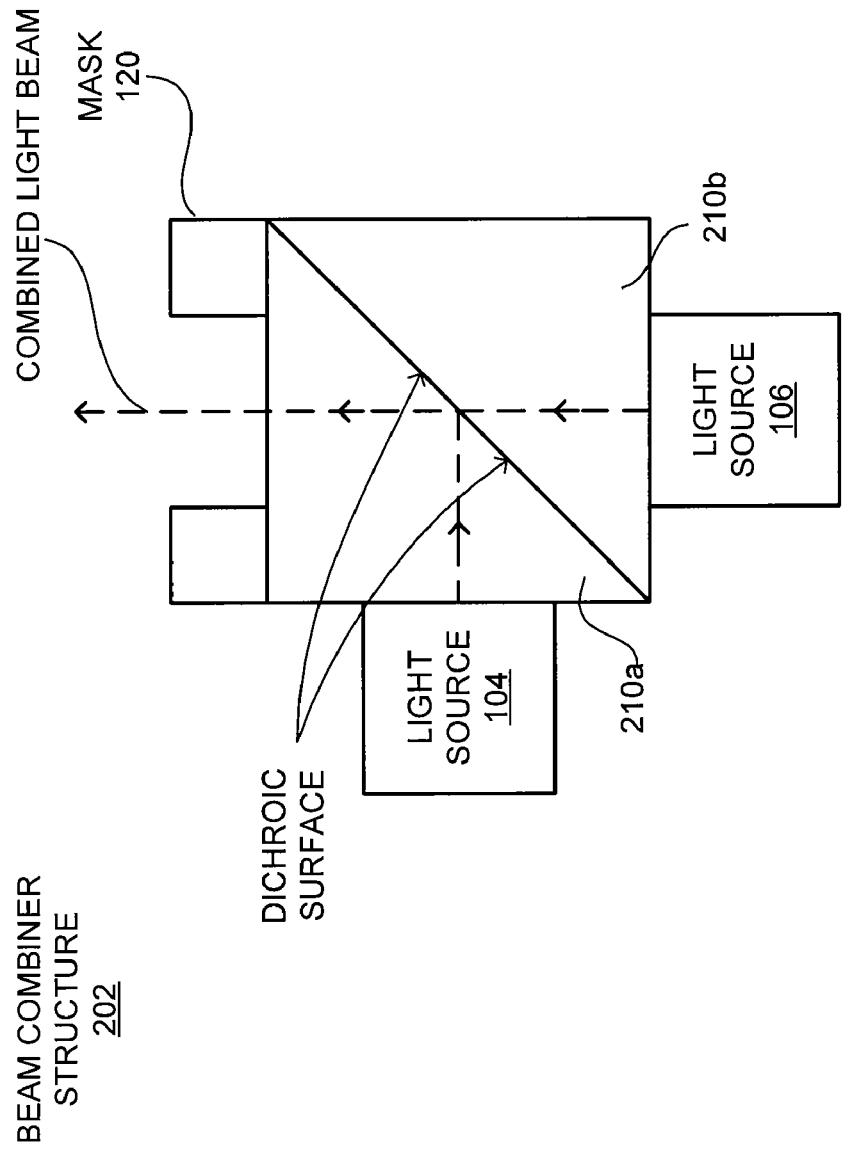
FIG. 2 illustrates an apparatus for combining light of two different wavelengths from two physically separate light sources, according to an embodiment of the present invention.

Referring to FIG. 2, the single dichroic surface reflects the wavelength generated by the light source 104 and passes the wavelength generated by the light source 106. Since only one dichroic surface is used, the assembly of prisms can be simplified. More specifically, the structure (also a cube in this example) can be made up of only two triangular prisms 210*a* and 210*b*.

Figure 3:
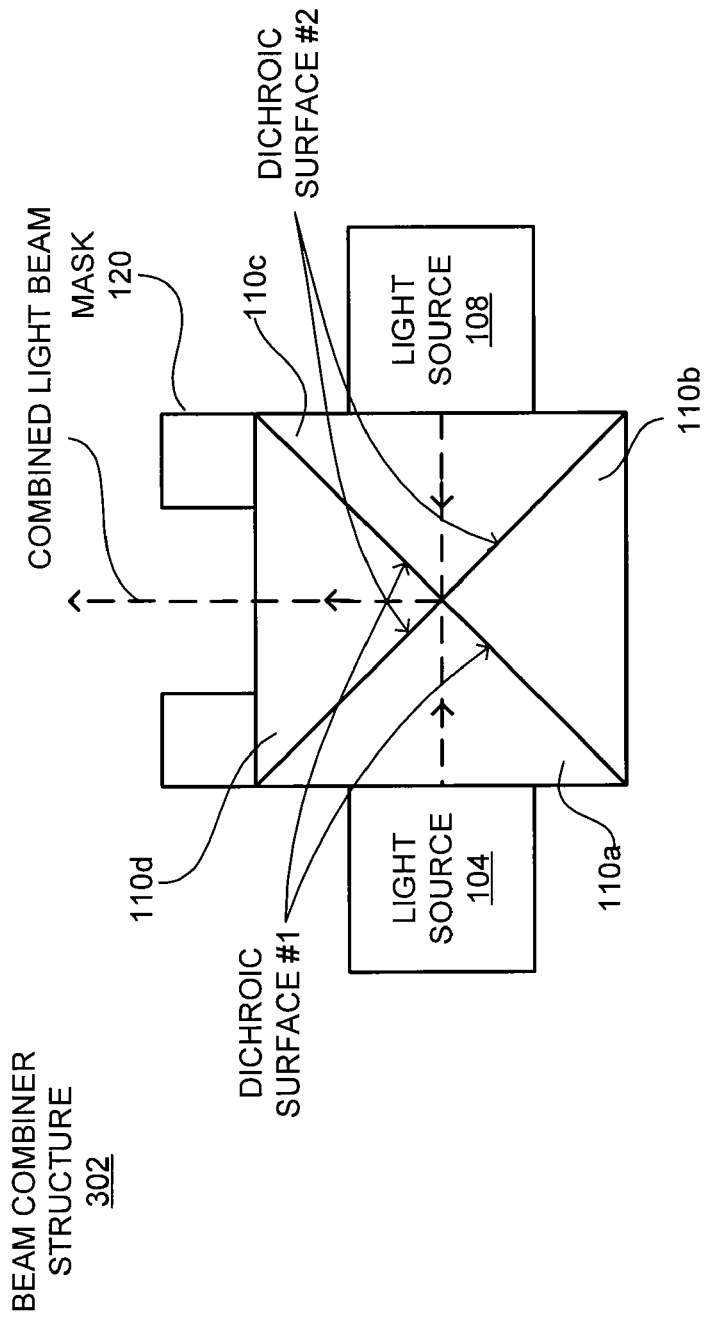
FIG. 3 illustrates an apparatus for combining light of two different wavelengths from two physically separate light sources, according to another embodiment of the present invention.
Figure 4:
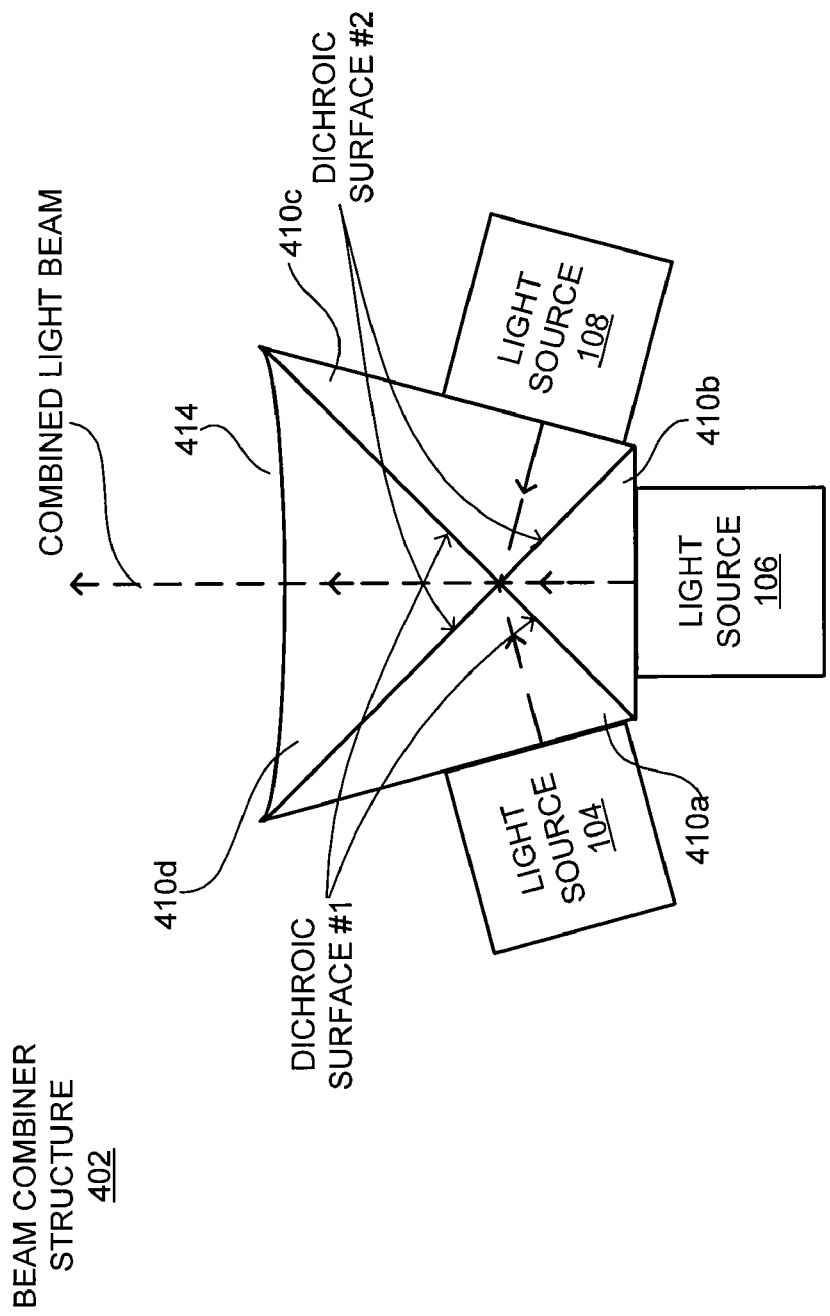
FIG. 4 illustrates an apparatus for combining light of three different wavelengths from three physically separate light sources, according to still another embodiment of the present invention.

In FIGS. 1, 2 and 3, the overall structures, formed from multiple prisms, were shown as being cubic. While embodiments of the present invention encompass such cubic structures, they should not be limited thereto. For example, other shapes, such as the ones shown in FIGS. 4 and 6, can be used. As can be seen from FIG. 4, the prisms 410*a*, 410*b*, 410*c* and 410*d* that make up the structure form a shape that resembles a trapezoid. Also shown in FIG. 4 is that not all outer sides of the structure need be flat. More specifically, in this example, the outer side 414 of prism 410*d*, through which the combined light beam travels, is shown as being concave, to increase the exit angle. Also shown in FIG. 4 is that not all of the prisms need be of the same size and shape.

Figure 5:
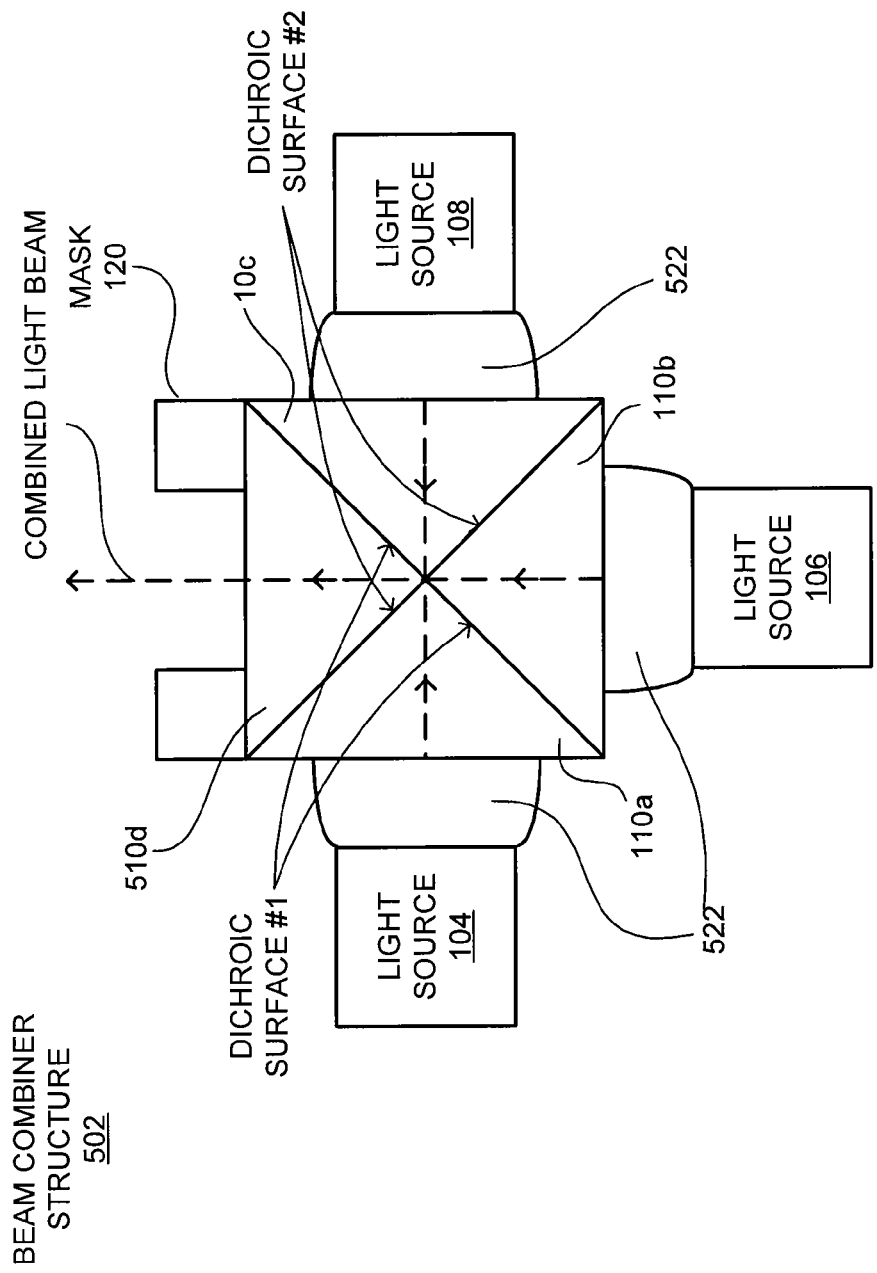
FIG. 5 illustrates an apparatus similar to the one shown in FIG. 1, but with the addition of combiner lenses between the light sources and prisms.

Referring now to FIG. 5, in accordance with an embodiment of the present invention, combiner lenses 522 can be added for reducing the emitted light angle before the light is combined by the dichroic surfaces. Such lenses 522 can be added in any of the embodiments described herein.

Figure 6:
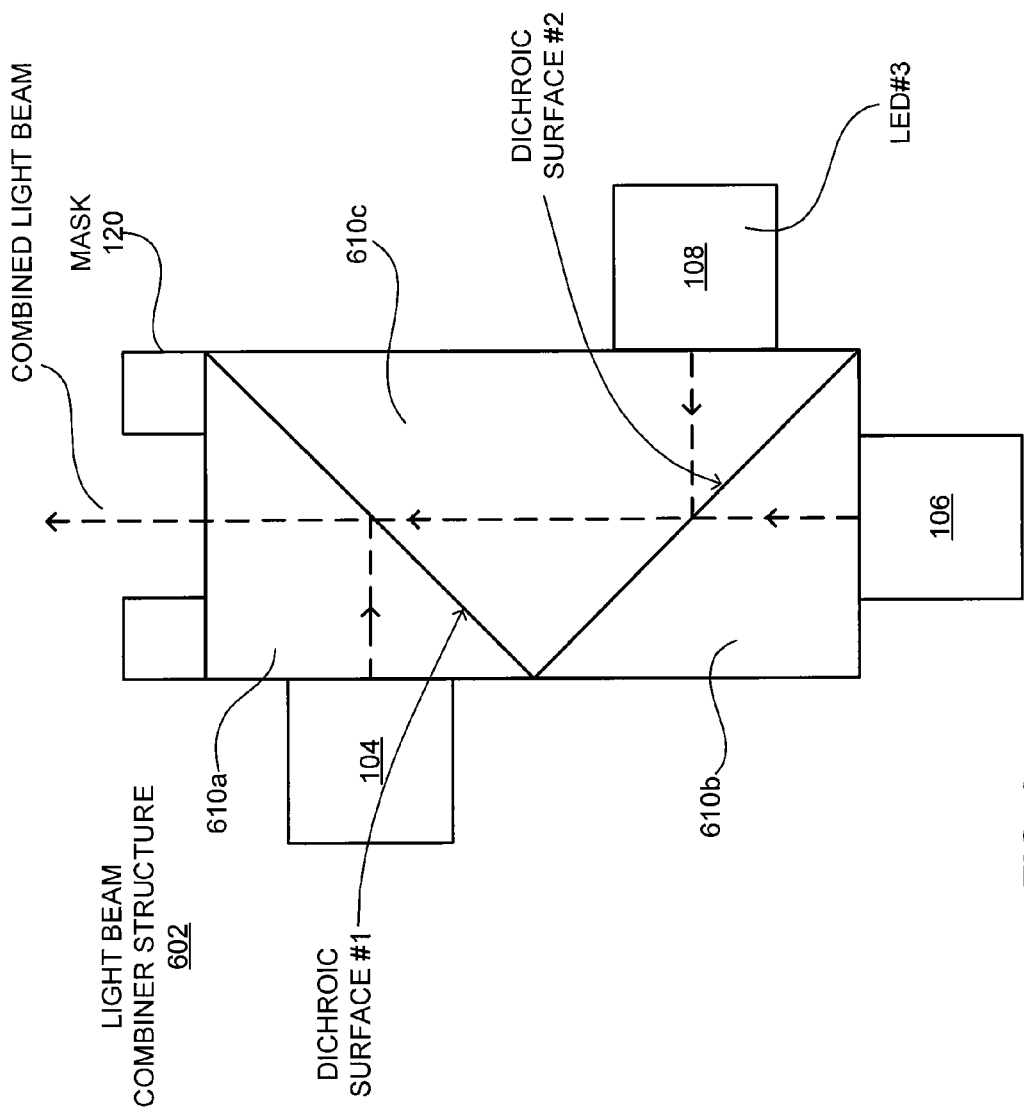
FIG. 6 illustrates an apparatus for combining light of three different wavelengths from three physically separate light sources, according to a further embodiment of the present invention.

FIG. 6 illustrates a variant of the present invention that has a simpler but likely somewhat larger overall size than the structure shown in FIG. 1. In this embodiment, only three prisms 610*a*, 610*b* and 610*c* are used to form a three-dimensional rectangular structure. Another difference is that the pair of dichroic surfaces do not intersect each other, as was the case in the previously discussed embodiments where there were three light sources. The beam combining structure 602 functions in a similar manner as the other structures discussed above. That is, dichroic surface #1 reflects the wavelength of light generated by the light source 104, and passes the wavelengths of light generated by the light sources 106 and 108. The dichroic surface #2 reflects the wavelength of light generated by the light source 108 and passes the wavelength of light generated by the light source 106. Because the light generated by the light source 104 is not incident upon the dichroic surface #2, it is not required that the dichroic surface #2 pass the wavelength generated by the light source 104, but it is allowed.

In the above discussed FIGS. 1 through 6, the dichroic surfaces were described as being formed on sides of prisms. The use of such structures is beneficial because the prisms can be bonded together to form a sturdy structure to which the light sources can be securely attached, as shown in the FIGS. However, in alternative embodiments, explained below with reference 7, this need not be the case.

Figure 7:
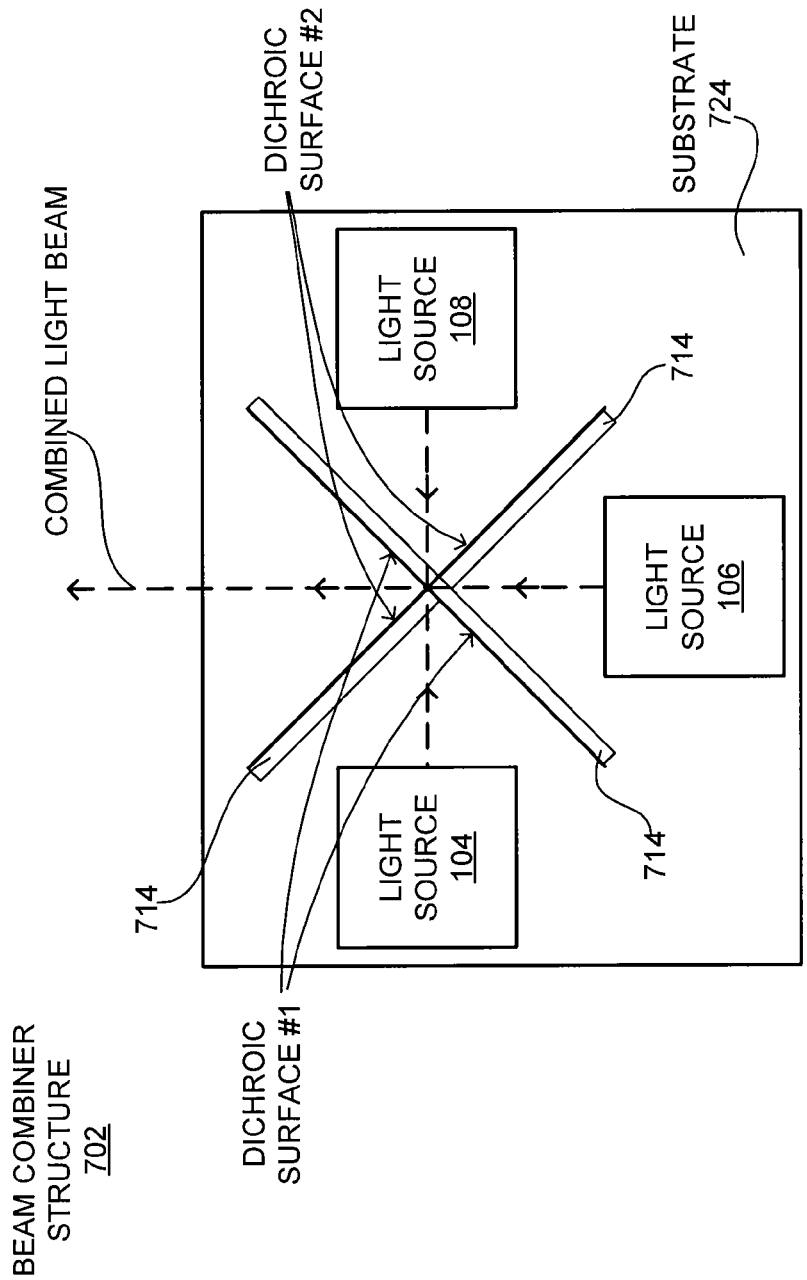
FIG. 7 illustrates how panels can be used in place of prisms.

Referring to FIG. 7, rather than using prisms, panels 714 are attached on at least one edge to a substrate 724, and dichroic surface(s) are formed on sides of the panels 714. While the panels 714 are likely made of glass, other suitable materials such as plastics may be used. (For FIG. 7, picture the substrate 724 being in the same plane as the page, and panels 714 extending perpendicularly out of the page.) In this embodiment, rather than securing the light sources 104, 106 and 108 to prisms, as could be done in the previously discussed embodiments, the light sources 104, 106 and 108 are secured to the same substrate 724 to which the panels 714 are secured. As was discussed above with reference to FIGS. 2 and 3, one of the light sources can be eliminated if two-wavelength pulse oximetry is to be used. Further, as was explained with reference to FIG. 2, if the light source to be eliminated is light source 104 or 108, then only one dichroic surface is required, which can be implemented using a single panel 714. In a similar manner as was described above with reference to FIGS. 4 and 6, the light sources and dichroic surfaces can be repositioned, so long as the arrangement results in the light of various wavelengths generally being combined into a single beam. Further, as was described with reference to FIG. 5, combiner lenses 522 can be added to the configuration shown in FIG. 7.

While the above described embodiments included either two or three separate light sources, one of ordinary skill in the art would understand, based on the above description, that light from more than three light sources can be combined in a similar manner. Accordingly, it is within the spirit and scope of the present invention that more than three light sources and more than two dichroic surfaces can be used. Such embodiments can be used for multi-wavelength oximetry that uses more than three wavelengths.

In accordance with other embodiments of the present invention, critical angle reflectors could be used instead of dichroic surfaces to accomplish combining of light from the two or more separate light sources. The critical angle is the largest angle off a surface at which light will be totally reflected from the surface. Sides of prisms or panels can positioned relative to light sources such that light of two or more wavelengths, from two or more separate light sources, can be combined into a single beam in much that same way as was described above with the use of dichroic surfaces.

Figure 8A:
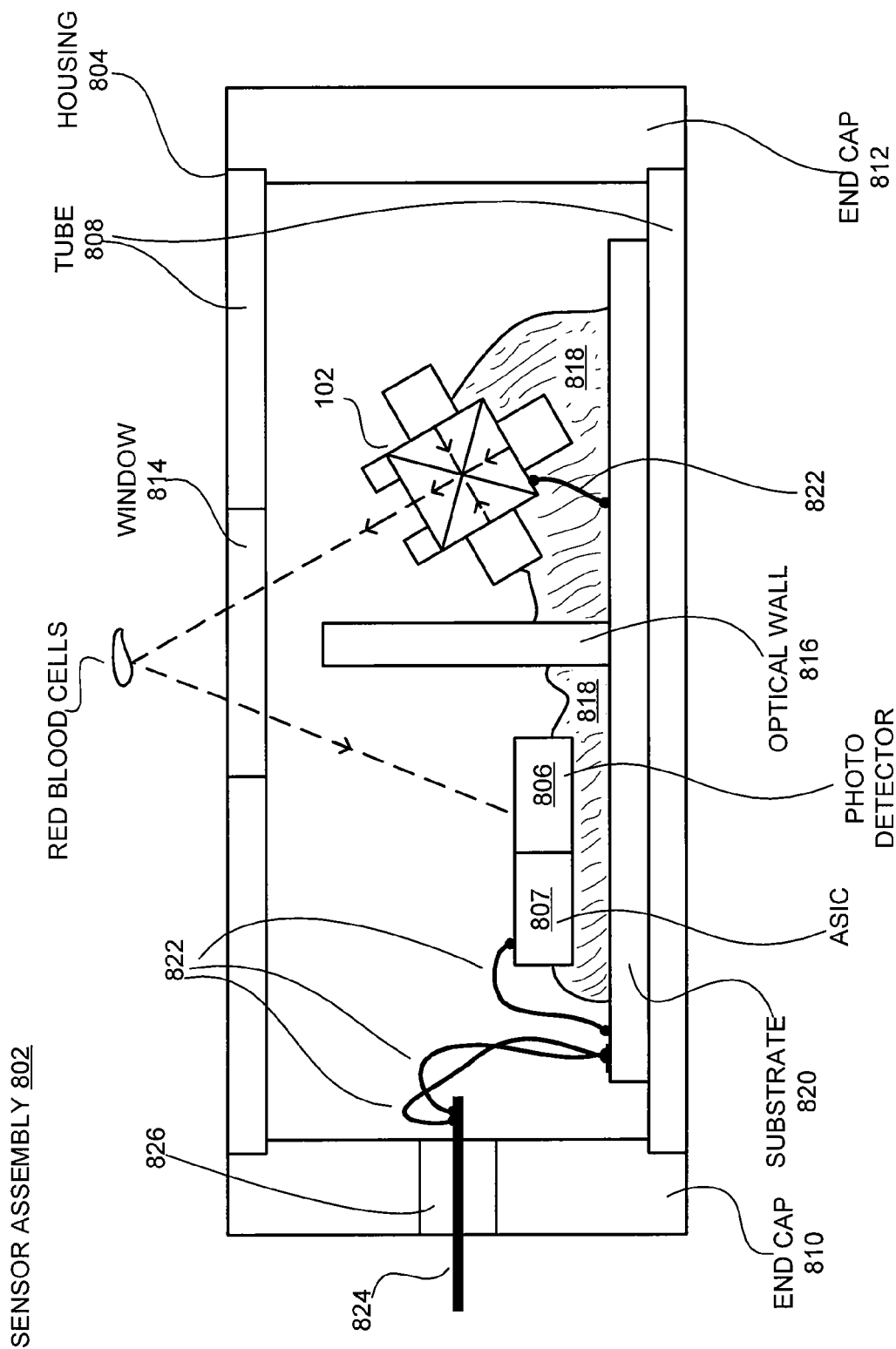
FIG. 8A illustrates an implantable oximetry sensor, according to an embodiment of the present invention.
Figure 8B:
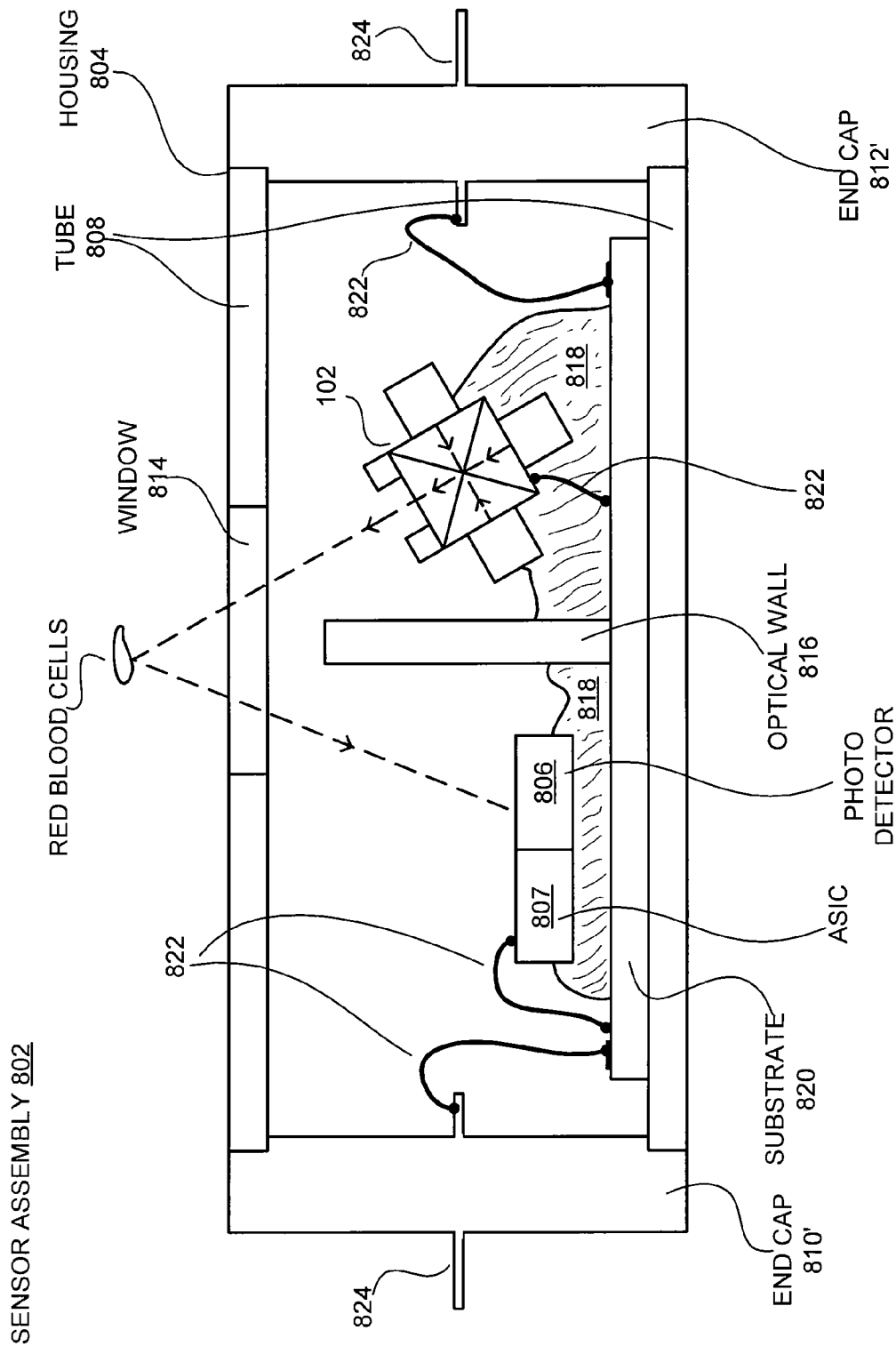
FIG. 8B illustrates an implantable oximetry sensor, according to another embodiment of the present invention.

In accordance with embodiments of the present invention, the beam combiner assemblies discussed above can be built into a sensor assembly 802, such as those shown in FIGS. 8A and 8B. The sensor 802, in turn, can be built into an implantable lead 902, such as that shown in FIG. 9.

Referring to FIG. 8A, in accordance with an embodiment of the present invention the sensor assembly 802 includes a sensor enclosure or housing 804 within which are one of the beam combiner structures discussed above, a photo detector 806 and an optional application specific integrated circuit (ASIC) 807. In FIG. 8A, the beam combiner 102 is shown. However, any of the other beam combiners 202, 302, 402, 502, 602 and 702 may alternatively be used. In accordance with an embodiment of the present invention, the housing 804 includes a tube 808 and a pair of end caps 810 and 812 that can be used to hermetically seal the components within the housing 802. The tube 808 can be made of an opaque material, such as metal (e.g., titanium or stainless steel) or ceramic, so long as it includes a window 814 that passes light of all the wavelengths of interest in the combined light beam (e.g., 130). In an alternative embodiment, the entire tube 808 can be made of a material that passes light of all the wavelengths of interest in the combined beam, and thus, in this embodiment the entire tube can be considered a window. The window 814 can for example be made of synthetic sapphire or some other appropriate material that passes light of all the wavelengths of interest. Alternatively, the entire tube 808 can be made from synthetic sapphire or some other appropriate material that passes light of all the wavelengths of interest. Exemplary synthetic sapphires are marketed by Imetra, Inc. (Elmsford, N.Y.) and Swiss Jewel (Philadelphia, Pa.).

The beam combiner structure (e.g., 102), the window 814 and the photo detector 806 should be positioned such that the combined light beam produced by the beam combiner exits the housing 804 through the window 814 and such that the light backscattered from blood (outside the window) will be scattered back toward the photo detector 806. The optional ASIC 807, which can include filters, analog-to-digital circuitry, multiplexing circuitry, and the like, controls the light sources and processes the photo detector signals produced by the photo detector 806 in any manner well known in the art. The ASIC 807 preferably provides digital signals indicative of the photo detector signals to an implantable device, such as an implantable monitor, pacemaker, or ICD. If the ASIC 807 or equivalent circuitry is not included within the sensor, analog signals can be delivered between the sensor 802 and the implantable device. However, it is preferred that digital signals are sent to and from the sensor 802 because digital signals are less susceptible to noise and other degradation.

An opaque optical wall 816 is positioned between the beam combiner structure 102 and the photo detector 806, so that light is not internally reflected from the beam combiner 102 to the photo detector 806. The beam combiner 102, optical wall 816, photo detector 806 and ASIC 807 can be attached to a substrate 820, e.g., by an epoxy 818. The substrate can be, e.g., a printed circuit board (PCB). Bond wires 822 can be used to attach the various components to the substrate 820, as well as to attach the substrate 820 to terminals 824 which extend through an insulated feedthrough 826 in the end cap 810. The housing 804, the feedthrough 826 and the endcaps 810 and 812 preferably provide hermeticity. In an alternative embodiment, shown in FIG. 8B, the endcaps 810' and 812' are made of a conductive material, and the tube 808 is made of a nonconductive material (so that the endcaps are electrically isolated from one another). In such an embodiment, there is no need for the feedthrough 826 shown in FIG. 8A because the terminals 824 can be connected directly to the conductive endcaps 810' and 812'. Nevertheless, a feedthrough may be used in the embodiment of FIG. 8B if desired.

Referring now to FIG. 9, in accordance with specific embodiments of the present invention, the sensor module 802 is built into an implantable lead 902. Accordingly, in this embodiment, the housing 804 of the sensor module 802 is sized to fit within the implantable lead 902. More specifically, the size of the beam combiner is preferably about 2 millimeters (mm) or less, and the size (shown as "d" in FIG. 10) of the sensor module 802 is about 4 mm or less, and preferably about 3 mm. The length of the sensor module 802, which extends axially in the lead 902 can be somewhat larger, because the length of the lead 902 is relatively large as compared to the diameter of the lead.

Further, the portion of the lead 902 that is adjacent to the window of the 814 of the sensor module, where light is to exit and enter, should allow the light to pass in and out of the sensor 802. Thus, the lead 902 may be transparent, or include its own window, opening, or the like. The lead 902 is shown as including tines 912 for attaching the lead in its desired position, but may include any other type of fixation means, or none at all. Additionally, the lead 902 may also include a lumen 916 for a stylet, which can be used for guiding the lead to its desired position. Also shown in FIG. 9 are wires 914 that provide power and possibly control signals to the sensor 802 from an implantable device, and provide pulse oxymetry signals from the sensor 802 to the implantable device. As discussed below, preferably there are only two wires 914, but there may be more. If the sensor 802 of FIG. 8B is used, then one wire 914 is attached to the terminal 824 that extends from the endcap 810', while another wire 914 is attached to the terminal 824 that extends from the other endcap 812'.

The lead 902 can be, e.g., an implantable right atrial lead for implant in a patient's right atrial appendage, a right ventricular lead for transvenous insertion into the heart, a coronary sinus lead for placement in the coronary sinus region, or some other lead. The lead 902 can be implanted in or near a patient's heart, but this is not necessary. The exemplary lead 902 shown in FIG. 9 is a right ventricular lead that includes a ring electrode 908 and a tip electrode 910 that are connected to an implantable device by way of wires 904 and 906. Instead of being placed in a lead that includes cardiac electrodes, the sensor can be within a catheter intended for placement in a blood vessel or other blood confining space.

Referring now to FIG. 10, which is a rough cross-sectional view along the dashed line shown in FIG. 9, in accordance with an embodiment of the present invention the tube portion 808 of the sensor housing 804 is generally "D" shaped, so that it can be readily included with the implantable lead 902, while still allowing the lumen 916 (for a stylet) and wires 904 and 906 to fit within the same inner-space of the lead 902. Alternative shapes are also within the scope of the present invention. If the sensor 802 of FIG. 8B is used, then one of the wires 914 would also be seen in the cross-section of FIG. 10.

After the ASIC 807 controls the light sources the processes signals produced by the photo detector 806 in a manner well known in the art, it delivers signals indicative of the intensity of the detected light to an implantable device, an example of which is discussed below with reference to FIGS. 15A and 15B. The implantable device further processes the signal, e.g., for diagnostic and/or therapeutic use. Preferably, the ASIC 807 has all electronics to provide a two-wire 914 digital interface to the implantable device, as shown in FIG. 9. Further, one of the two sensor wires 914 may be combined with one of the pacing electrode wires 904 or 906 so that only three total wires are needed. Even further, a more complex 2-wire approach could use sub-pacing threshold signals between the implantable device and the sensor 802 using the same two wires 904 and 906 that connect to the pacing electrodes 908 and 910 resulting in a total of two wires in the lead 902 to the implantable device.

The lead 902 within which the sensor 802 is contained is attached to an implantable device. It is also possible that the sensor 802 is within a self contained hermetically sealed housing that communicates wirelessly with the implantable device. As mentioned above, the implantable device can be, e.g., a monitor, pacemaker, or ICD. For completeness, an exemplary implantable device 1510, that can be used to perform pacing, detect an arrhythmia, perform anti-arrhythmia therapy, detect specific cardiac events, etc., is described with reference to FIGS. 15A and 15B.

In accordance with embodiments of the present invention, the components are hermitically sealed within the sensor 802. Preferably the only elements running to and from the sensor 802 are wires 914 for providing power and possibly control signals to the sensor 802, and receiving pulse oxymetry signals from the sensor 802.

In accordance with other embodiments of the present invention, the oxymetry sensor module 802 is located within the housing of an implantable device that includes a window through which light can be transmitted and received. In still another embodiment, the oxymetry sensor module 802 is in its own hermetically sealed housing that is attached directly to an implantable cardiac device. Additional details of how this can be accomplished are provided in commonly assigned U.S. patent application Ser. No. 10/913,942, entitled "Autonomous Sensor Modules for Patient Monitoring" (Turcott et al.), filed Aug. 5, 2004, which is incorporated herein by reference.

As mentioned above, the ASIC 807 (and/or other circuitry) controls the light sources and processes signals produced by the photo detector 806, as well as delivers signals indicative of the intensity of the detected light to an implantable device, an example of which is discussed below with reference to FIGS. 15A and 15B. The implantable device further processes the signal, e.g., for diagnostic and/or therapeutic use. For example, the implantable device can include a microcontroller that determines levels of blood oxygen saturation and/or hematocrit based on the signals it receives from the photo detector 806. Such measures of oxygen saturation can be used, e.g., for pacing optimization, disease monitoring, and the like. Additionally or alternatively, the measures of oxygen saturation can be stored in memory for later transmission to an external device.

As also mentioned above, the ASIC 807 (and/or other circuitry) can include filters, analog-to-digital circuitry, multiplexing circuitry, and the like, to control the light sources and process the photo detector signals produced by the photo detector 806. The ASIC 807 preferably provides digital signals indicative of the photo detector signals to an implantable device, such as an implantable monitor, pacemaker, or ICD. If the ASIC 807 or equivalent circuitry is not included within the sensor, analog signals can be delivered between the sensor 802 and the implantable device. However, it is preferred that digital signals are sent to and from the sensor 802 because digital signals are less susceptible to noise and other degradation. It is also possible, as mentioned above, that the sensor module 802 is located within the housing of an implantable device that includes a window through which light can be transmitted and received, or that the sensor module 802 is in its own hermetically sealed housing that is attached directly to an implantable cardiac device.

Each light source (e.g., LED) transmits light in response to being driven by a drive signal, which is typically a current signal, but can be a voltage signal. As the light sources age they become less efficient in that for a same drive signal they will transmit light of less intensity. If not compensated for, this will effect the intensity of the light detected by the photo detector 806, which will in turn adversely effect determinations of blood oxygen saturation, etc. In accordance with specific embodiments of the present invention, to overcome this problem, a calibration photo detector 1106 is added, the output of which is used to compensate for aging or other changes to the light source(s), as will now be described with reference to FIG. 11A.

Figure 11A:
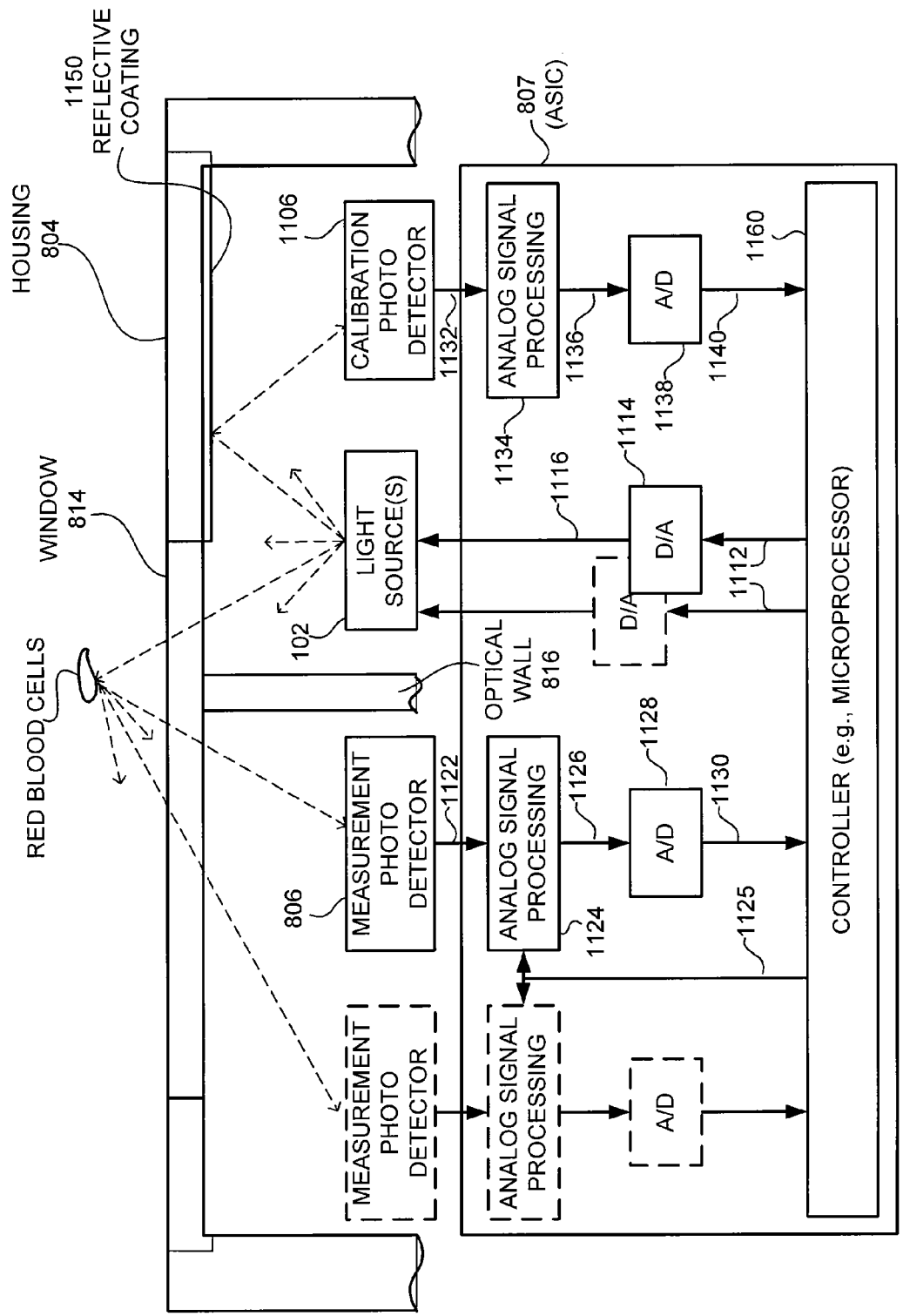
FIGS. 11A and 11B illustrate implantable self-calibrating sensors, according to specific embodiments of the present invention.

FIG. 11A shows additional details of the ASIC 807, in accordance with specific embodiments of the present invention. However, it should be noted that the circuitry shown in FIG. 11A need not be implemented within the ASIC 807. For clarity, the photo detector 806 that detects light scattered back into the housing 804 through the window 814 will often be referred to hereafter as the measurement photo detector 806, and the added photo detector 1106 that is used to compensate for changes in the light sources (e.g., due to aging) will be referred to as the calibration photo detector 1106. Additionally, when discussing FIG. 11A, the beam combiner structure 102 will often be referred to simply as light source(s) 102, because the embodiments that relate to compensation can be used with a single light source, or with a device that does not necessarily use the specific beam combiners described above, or even with multiple light sources without a beam combiner. Nevertheless, the embodiments described with reference to FIG. 11A would be very useful with the beam combiners described above.

Referring to FIG. 11A, each light source transmits light having an intensity that is controlled by a corresponding drive signal 1112/1116. Such drive signal is controlled by a controller 1160, which likely outputs a digital drive control signal 1112 which is converted to an analog drive signal 1116 by a digital-to-analog converter (D/A) 1114. The controller 1160 in this embodiment, and other embodiments, can be a microcontroller, a processor, a state machine, random logic, or the like. The light output by the light source(s) is projected over a wide range of angles (e.g., from 120 degrees to 180 degrees). Accordingly, a portion of this light exits the housing 804 through the window 814, while other portions of the light are internally reflected.

As explained above, the opaque optical wall 816 is positioned between the light source(s) 102 and the measurement photo detector 806, to prevent the measurement photo detector 806 from detecting internally reflected light. (It is noted, that due to imperfections, the measurement photo detector 806 may detect a small amount of internally reflected light, which is allowed). In contrast, the calibration photo detector 1106 is placed on the same side of the wall 816 as the light source(s) 102, and positioned relative to the window 814 such that the calibration photo detector 1106 detects internally reflected light from the light source(s) 102 without detecting light that is scattered back into the housing 804 through the window 814. (It is noted, that due to imperfections, the calibration photo detector 806 may detect a small amount of scattered light, which is allowed). Alternatively, the region of the window above the calibration photo detector 1106 can have a blocking or a reflecting coating such that the calibration photo detector 1106 generally only detects internally reflected light from the light source(s) 102. It is also possible that the calibration photo detector 1106 is arranged such that it detects light transmitted directly from the light source(s) 102, i.e., the light need not be internally reflected. For simplicity, the window 814 in FIG. 11A and the previously described FIGS. has been generally shown as a single portion through which light of interest can enter and exit the housing 804. However, it is noted that such window 814 can be made up of more than one distinct portion through which light of interest can enter and exit the housing 804. For example, light may exit the housing 804 through a first portion of the window 814, while scattered light enters the housing 804 through a second portion of the window 814, where the first and second portions of the window are not contiguous. In other words, the term window 814, as used herein, is intended to collectively encompass all portions of the housing through which light can enter and exit the housing, even if such portions are separated from one another (e.g., by opaque portions).

In the above arrangement of FIG. 11A, the measurement photo detector 1106 detects light scattered back into the housing 804 through the window 814, and produces a measurement signal 1122 that is indicative of the intensity of the light detected by the measurement light detector 1106. The measurement signal 1112 is preferably filtered and amplified by an analog signal processing block 1124 (e.g., which includes a filter and amplifier), and digitized by an analog-to-digital (A/D) converter 1128, so that a digitized version 1130 of the signal is provided to the controller 1160.

The calibration light detector 1106, on the other hand, detects a portion of the light transmitted by the light source(s) that has not exited the housing 804 (e.g., the light is internally reflected and/or received directly from the light source(s)), and produces a calibration signal 1132 that is indicative of the intensity of such detected light. The calibration signal 1132 is preferably filtered and amplified by an analog signal processing block 1134 (e.g., which includes a filter and/or amplifier) and digitized by an analog-to-digital (A/D) converter 1140, so that a digitized version 1140 of the signal is provided to the controller 1160.

In FIG. 11A, a separate D/A converter 1114 and drive signal 1112 are shown for each light source. In an alternative embodiment, the controller can output a time multiplexed drive signal 1112 that is provided to a single D/A converter 1114, and a demultiplexer can be provided at the output of the D/A converter 1114. Such a demultiplexer will provide the analog version of the drive signal to the appropriate light source. Similarly, in FIG. 11A the measurement photo detector 806 is shown as having its own analog signal processing block 1124 and A/D converter 1128, and the calibration photo detector 1106 has its own analog signal processing block 1134 and A/D converter 1138. In an alternative embodiment, a multiplexer is provided at the outputs of the detectors 806 and 1106 so that a single analog signal processing block and A/D converter can be used. In other words, such a multiplexer can be provided between a single analog signal processing block and the detectors 806 and 1106. Such embodiments would reduce the circuitry, e.g., of the ASIC 807.

The calibration signal 1132, or the filtered, amplified and digitized version thereof (i.e., 1140), is used to compensate for changes to the lights source(s) 102, e.g., due to aging, as will be described below. For example, in specific embodiments, the controller 1160, adjusts the drive signal 1112, based on the intensity of the light detected by the calibration photo detector 1106, in order to keep the intensity of light transmitted by a light source substantially constant. More specifically, the controller 1160 adjusts the drive signal 1112, based on the calibration output signal 1132, or the filtered, amplified and digitized version thereof (i.e., 1140), to keep the intensity of the light transmitted by each light source substantially constant. Where there are two or more light sources, this does not necessarily mean that all the light sources will be kept at a same substantially constant intensity. Rather, this means that the intensity of each individual light source is kept substantially constant, but that the intensity of one light source can be different than the intensity of another light source. In a specific embodiment, the intensity of light transmitted by a light source is kept substantially constant by adjusting the drive signal 1112 in an effort to keep the portion of the calibration signal 1132 corresponding to that light source at a specified level.

In alternative embodiments, rather than adjusting the drive signals 1112 to compensate for changes to the lights source(s) 102, adjustments are made to the measurement signal 1122 to compensate for changes in the intensity of the light source(s) 102. This can be accomplished as follows. The controller 1160 detects changes (likely reductions) in the intensity of the light source(s) 102 by detecting changes in the calibration signal 1132, or the filtered, amplified and digitized version thereof (i.e., 1140), in a similar manner as was discussed above. Then, based on the changes in the calibration output signal 1132, or the filtered, amplified and digitized version thereof (i.e., 1140), the controller 1160 adjusts the measurement signal 1122. This can be accomplished, e.g., by using a gain adjustment signal 1125 to adjust the gain of an amplifier within the analog signal processing block 1124. For example, if the controller detects a 5% reduction in the intensity of light of a specific wavelength (i.e., light from a specific light source) based on the calibration signal 1132, the controller can increase the gain in an amplifier of the analog signal processing block 1124 by 5%

In still other embodiments, rather than adjusting actual signals (e.g., a drive signal or measurement signal), a processor algorithmically compensates for changes to the intensity of the lights source(s) 102. More generally, a processor that uses the measurement signal 1122 (for a diagnostic and/or therapeutic purpose), detects changes in the intensity of the light transmitted by each light source based on the calibration signal, and the processor takes into account such changes in intensity when using the measurement signal for its diagnostic and/or therapeutic purpose. For example, if the controller detects a 5% reduction in the intensity of light of a specific wavelength (i.e., light from a specific light source) based on the calibration signal 1132, the processor can take such reduction into account when determining levels of blood oxygen saturation and/or levels of hematocrit. For example, if the processor uses a multi-dimensional lookup table to determine levels of blood oxygen saturation, based on the intensity of detected scattered light, the processor can adjust where to look in the look-up table based on changes in the calibration signal. For another example, if the processor uses an algorithm to determine levels of blood oxygen saturation, based on the intensity of detected scattered light, the processor can make adjustments to the algorithm based on changes in the calibration signal. These are just a few examples of how a processor can take into account changes in the intensity of the calibration signal when using the measurement signal for a diagnostic and/or therapeutic purpose. In specific embodiments, the processor that uses the measurement signal for its diagnostic and/or therapeutic purpose is in a separate implantable housing that is connected to the housing 804 by one or more lead. For example, the processor can be within a housing of a stimulation device (e.g., device 1510 of FIG. 15A).

As mentioned above, in additional to using the above described sensors to measure levels of blood oxygen saturation, such sensors can also be used to measure levels of hematocrit, which refers to the percentage of packed red blood cells in a volume of whole blood. Various techniques are known for determining hematocrit based on scattered light. For example, light of about 500 nm and light of about 800 nm can be directed at a blood sample, and an algorithm can be used to calculate hematocrit based on the intensities of detected scattered light. In another technique, a pair of spatially separated photo detectors can be used to detect reflected infra red (IR) light, e.g., of 805 nm. The intensity of the IR light detected by the photo detector that is nearer to the IR light source is referred to as IRnear, and the intensity of the IR light detected by the photo detector farther from the IR light source is referred to as IRfar. As described in article by Bornzin et al., entitled "Measuring Oxygen Saturation and Hematocrit Using a Fiberoptic Catheter", *IEEE/9th Annual Conf. of the Eng. & Biol. Soc.* (1997), which is incorporated herein by reference, the ratio: R=IRnear/IRfar is directly related to the level of hematocrit, but independent of oxygen saturation because 805 nm is an isobestic wavelength. To implement this technique using the sensor configuration shown in FIG. 11A, a second measurement photo detector 806 (shown in dashed line) can be added, with the second measurement photo detector being further from (or closer to) the light source(s) 102 than the other measurement photo detector 806. This second measurement photo detector can have its own corresponding analog signal processing block and A/D converter, or such circuitry can be shared (e.g., multiplexed) with the other measurement photo detector. The above described embodiments of the present invention can be used to compensate for changes in the intensity of the IR light source, e.g., due to aging. In specific embodiments of the present invention, the second measurement photo detector is placed within the housing 804 as shown in FIGS. 8A, 8B, 9 and 10, thereby enabling levels of hematocrit to be measured without the need for relatively large fiber optic guides, use of which was taught in the above mentioned Bornzin et al. article. For example, referring back to FIGS. 8A, 8B, 9 and 10, such second measurement photo detector can be located farther from the optical wall 816 than the photo detector 806 shown, as can be appreciated from FIG. 11A.

Figure 11B:
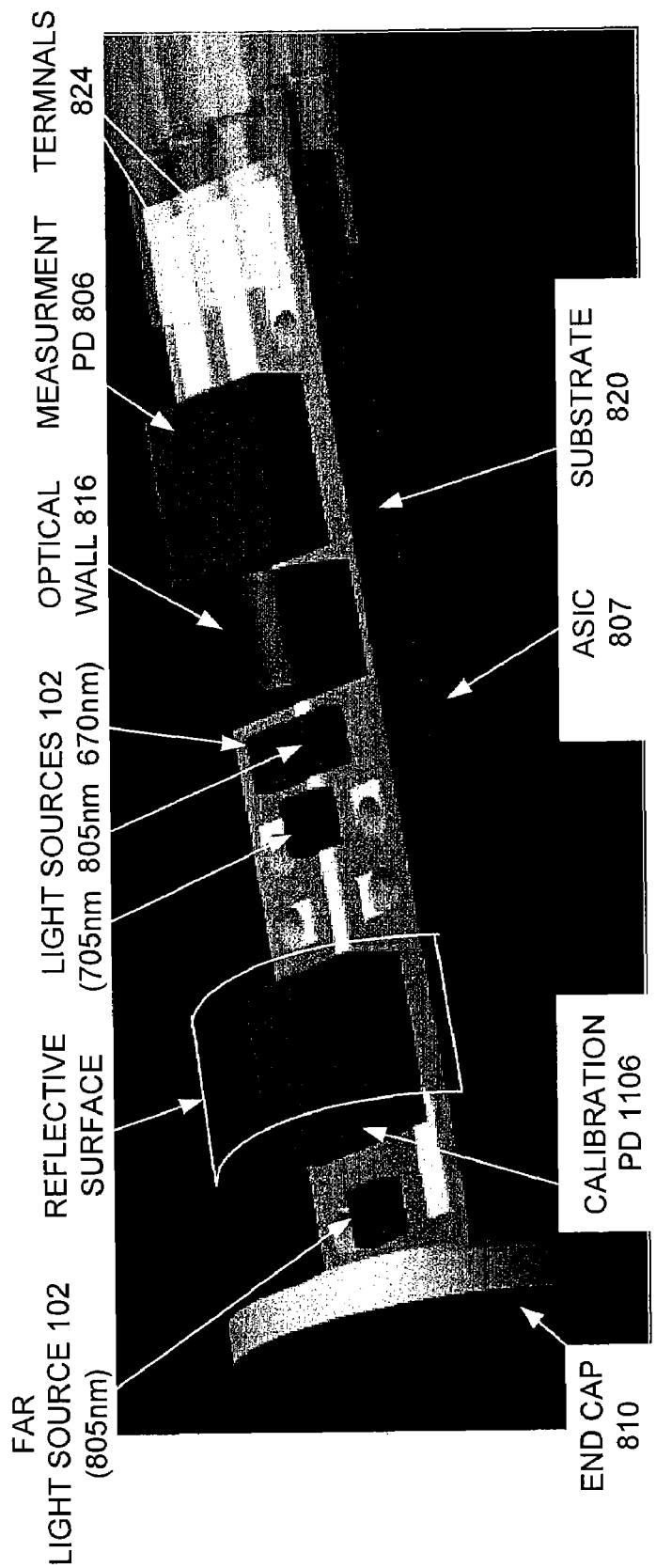

In an alternative embodiment, rather than having two spatially separated measurement photo detectors, two light sources (e.g., two 805 nm LEDs) can be spatially separated and time multiplexed, with one light source being closer to the measurement photo detector 806 than the other. In this alternative embodiment, the same ratio R=IRnear/IRfar can be determined, with the IRnear corresponding to scattered light originating from the LED that is closer to the measurement photo detector 806, and the IRfar corresponding to scattered light originated from the LED farther from the measurement photo detector 806. An example of this is shown in FIG. 11B, which shows an exemplary layout of elements that can be inserted into a sealed tube 808 (not shown in FIG. 11B), as described above in the discussion of FIG. 8A. Using a pair of spatially separated 805 nm light sources is advantageous, as compared to using a pair of spatially separated measurement light detectors, because light sources (such as LEDs) are typically significantly smaller than photo detectors, thus resulting in space savings. As with the previously described embodiments, the calibration photo detector 806 will detect internally reflected light from the near and far light sources 102, and the measurement photo detector 806 will detect scattered light from the near and far light sources 102.

Combinations of the embodiments that compensated for changes in light intensity are also within the scope of the present invention. For example, it may be that the drive signal 1112 is only increased when the intensity of a light source has decreased by a specific level, and that up to that point a processor performs any necessary compensation algorithmically. This is just one example of how embodiments can be combined, which is not meant to be limiting. It is also noted that the embodiments that compensate for changes in the intensity of light produced by one or more implanted light source can also be used with implantable photo plethysmography (PPG) devices, such as, but not limited to those described in the following commonly assigned patents and application, each of which are incorporated herein by reference: U.S. Pat. No. 6,491,639 (Turcott); U.S. Pat. No. 6,561,984 (Turcott); U.S. Pat. No. 6,731,967 (Turcott); U.S. Pat. No. 6,942,622 (Turcoft); and U.S. patent application Ser. No. 10/764,419 (Turcott), filed Jan. 23, 2004.

Referring again FIG. 11A, each time light is transmitted from the light source(s) 102, light that exits the window 814 and thereafter enters the window (after being scattered by blood) will impinge on the measurement photo detector(s) 806, and internally reflected light that has not exited the housing 804 will impinge on the calibration photodetector 1106. Thus, a calibration signal is produced by the calibration photodetector 1106 whenever a measurement signal 1122 is produced by the measurement photodetector 806, and the calibration signal can be measured and used to perform any of the above described calibrations whenever a measurement signal 1122 is produced by the measurement photodetector 806. While this may result in the most up-to date calibrations, this would consume more processing resources and battery power than typically necessary or desired. More specifically, because changes in the intensity of the light output by the light source(s) 102 (e.g., due to age) will occur relatively slowly (i.e., over relatively long periods of time), calibrations to compensate for such changes in the light intensity need not be performed at all times. Rather, in accordance with certain embodiments of the present invention, battery power and processing resources are conserved by only performing such calibrations from time-to-time (e.g., once a month, or the like).

Producing or taking a calibration measurement, as the phrase is used herein, refers to measuring the magnitude of the calibration signal 1132 produced by the calibration photo detector. Such a calibration measurement can thereafter be used for performing a calibration. Preferably, a calibration measurement is indicative of an average magnitude of the calibration signal over a specified period of time (e.g., a few minutes). This can be accomplished, e.g., by integrating, averaging or otherwise combining sample data of the calibration signal collected over a period of time.

Performing a calibration, as the phrase is used herein, refers to compensating for a change (typically a depletion) in the intensity of light transmitted by a light source 102. A calibration can always be performed based on a recently obtained calibration measurement. Alternatively, calibrations can be performed more often than calibration measurements. For example, a calibration measurement may only be taken once every three months, but a calibration can be performed once a month, e.g., by predicting what a calibration measurement would be, between actual calibration measurements. Such predictions can be, e.g., based on previous measurements. For example, as will be described with reference to FIGS. 12A-12C, a depletion curve for a light source can be determined based on previous calibration measurements, and an algorithm can be determined for the curve and used to predict calibration measurements, or to otherwise predict the intensity of light transmitted by the light source between calibration measurements.

Various systems and methods for performing calibrations were described in detail above. Referring to FIG. 11, in certain embodiments, the controller 1160 adjusts a drive signal 1112 (that drives a light source 102, e.g., LED), based on the calibration signal 1132 produced by the calibration photodetector 1106, to keep the intensity of the light transmitted by the light source 102 substantially constant. In other embodiments, the controller 1106 adjusts the measurement signal 1122 (produced by a measurement light detector 806), based on the calibration signal, to compensate for changes in the intensity of the light transmitted by the light source. In still other embodiments, a processor that uses the measurement signal (produced by the measurement light detector 806) for a diagnostic and/or therapeutic purpose (e.g., to determine levels of blood oxygen saturation and/or levels of hematocrit), detects changes in the intensity of the light transmitted by each light source based on the calibration signal, and the processor takes into account the changes in intensity when using the measurement signal for the diagnostic and/or therapeutic purpose. Performing each of the above described types of calibrations consumes battery power and/or processing resources. Additionally, taking calibrations measurements also consumes battery power and/or processing resources. Thus, it is beneficial to reduce and preferably minimize calibration measurements and performing calibrations, while maintaining the improvements in accuracy that can be achieved using such calibrations.

In specific embodiments, a calibration measurement is produced periodically, e.g., once a month, and a calibration is performed with the same periodicity. In other words, a calibration may only be performed when a new calibration measurement is made. Alternatively, one or more calibration can be performed between successive calibration measurements, e.g., using extrapolation or the like. For example, the controller 1160 can update the drive signal 1112 (that drives a light source 102, e.g., LED) once a month, to keep the intensity of the light transmitted by the light source 102 at a desired level. For another example, the controller can adjust the measurement signal 1122 (produced by the measurement light detector 806) to compensate for changes in the intensity of the light transmitted by the light source 102, by adjusting the gain of an amplifier within the analog signal processing block 1124, once a month. In still another example, an algorithm or lookup table that is used to determine levels of blood oxygen saturation and/or levels of hematocrit can be updated once a month, to compensate for changes in the intensity of the light transmitted by the light source 102. For each of the above examples of performing a calibration, a calibration measurement can be made once a month, and that measurement can be used to perform a calibration. Alternatively, a calibration measurement can be taken only once every three months, yet a calibration can still be performed every month using extrapolation, or the like. More generally, as mentioned above, calibrations can be performed more often than calibration measurements.

The time between producing successive calibration measurements and/or between performing successive calibrations can be predetermined, and programmed into an implantable device. In other embodiments, the time between successive calibration measurements and/or performing calibrations can be based on dynamic factors. For example, the implantable device can track how long a light source has been cumulatively transmitting light since a last calibration. For example, if a light source transmits light for 1 msec, once every second, then it would take 1000 seconds for the light source to have cumulatively transmitted light for 1 second. This can be kept track of such that a calibration measurement is taken whenever the cumulative time since the last calibration reaches a threshold (e.g., until the time of cumulatively transmitted light reaches 1000 hours). If the light source always transmits light for the same amount of time (e.g., 1 msec) every time the light source is turned on, then a simple counter can be used to keep track of how long the light source has cumulatively transmitted light. Such a counter can be incremented every time the light source it turned on. Such embodiments are especially useful where the use of the light source varies. However, if the light source is always going to be turned on for 1 msec, once every second, then it may be simpler to produce a new calibration measurement at a fixed period (e.g., one every three months). However, where the light source is used more intermittently, and less predictably, it is quite useful to keep track of a parameter, such as how long the light source has cumulatively transmitted light since the last calibration measurement.

The total cumulative amount of time a light source has transmitted light is relevant when tracking depletion of the intensity of the light transmitted by the light source. Additionally, the amount of current used to drive the light source will also affect the light source's depletion. Accordingly, in embodiments where the magnitude of the drive signal 1112 changes, such magnitude can be used as a weighting factor where the cumulative amount of time a light source has transmitted light is being tracked. Thus, increases in the magnitude of the drive signal 1112 may cause calibrations measurements to be taken more frequently, to compensate for the depletion of the intensity of the light source occurring more rapidly due to the use of a higher drive current. Additionally, or alternatively, increases in the magnitude of the drive signal 1112 can be taken into account when performing calibrations.

In accordance with specific embodiments, the controller 1160 can detect a change in the intensity of light output by each light source by comparing a present calibration measurement ($Cal_{Tn}$) to a previous calibration measurement ($Cal_{T(n-1)}$). For example, a percentage reduction in intensity can be computed using the equation: % change in intensity= $(Cal_{T(n-1)} - Cal_{Tn})/(Cal_{T(n-1)})$. Similarly, a ratio representative of a change in the intensity of light output by each light source can be computed using the equation: ratio= $(Cal_{T(n-1)})/(Cal_{Tn})$.

Such % changes in intensity or ratios can thereafter be used to adjust each drive signal that is used to drive a light source, to adjust a measurement signal produced by a measurement light detector, and/or to adjust algorithms, look-up tables, or the like, as described above. For example, where the % change in intensity is a 10% reduction, the drive signal can be increased by 10%, the measurement signal can be increased by 10%, or the value of the measurement signal used in an algorithm can be increased by 10%. Similarly, where the ratio representative of the change in the intensity of light is 9/10, the drive signal can be multiplied by 10/9, the measurement signal can be multiplied by 10/9, or the value of the measurement signal used in an algorithm can be multiplied by 10/9. The calibration ratio can be k*10/9 if the relationship between light and current is weighted (with k being a weighting factor) or f(i)*10/9 where i is the drive current.

Where a sensor includes more than one light source 102, each light source 102 may get depleted at a different rate. In such embodiments, a separate measurement signal and calibration signal is produced for each light source 102, so that different calibration measurements can be produced and different calibrations can be performed for each light source 102.

In accordance with certain embodiments, to reduce effects of noise and potential erroneous signals, the calibrations signal (and measurements thereof produced for each light source is averaged over a specified period of time, which can be, e.g., preset or programmed, to produce calibration measurements. For example, in specific embodiments, for each light source 102, a certain amount of calibration data is collected starting at a time T1 and averaged to produce a calibration measurement $Cal_{T1}$. Starting at a later time, T2, the same amount of calibration data is collected and averaged to produce a calibration measurement $Cal_{T2}$. Thereafter, from time T2 to a next calibration time T3, the ratio $Cal_{T1}/Cal_{T2}$ can be used to perform calibrations. Similarly, from time T3 to a next calibration time T4, the ratio $Cal_{T1}/Cal_{T3}$ (i.e., $Cal_{T1}/Cal^{T2}*Cal_{T2}/Cal_{T3}=Cal_{T1}/Cal_{T3}$) can be used to perform calibrations. In a similar manner as discussed above, weighting factors can be used, if desired.

A reduction in the intensity of light produced by a light source 102 will also be referred to herein as depletion. In certain embodiments, a trend of depletion, also referred to as a depletion curve, can be established by producing calibration measurements at several points in time for each light source 102 or, if available from a manufacturer, a known calibration curve can be used by programming the equation of the curve into the device. The established or known depletion curves can then be used to perform calibrations between calibration measurements. An example of a typical LED depletion curve 1202 is shown in FIG. 12A. Referring to FIG. 12B, if a calibration measurement is taken at time T1, then at time T2, an equation for the depletion curve can be established (e.g., y=mx+b). This can be appreciated from FIG. 12C, which is a zoomed in view of the portion 1204 of the curve 1202 shown in FIG. 12B. Between times T2 and T3, the equation can be applied to estimate all of the points on the calibration curve 1202 without taking a calibration measurement. At time T3, another calibration measurement can be taken and a new equation can be established based on the measurements at times T2 and T3, or based on all the previous measurements, i.e., at times T1, T2, and T3. From T3 to T4, this new equation can be applied, etc.

If the depletion curve is truly linear, the equation should be almost the same each time, but calculating it will ensure that no unusual change has taken place in the performance of the light source. Since a depletion curve of an actual light source is not truly linear, extrapolation is useful, as is adjusting the frequency of calibration measurements, depending upon the depletion rate. For example, if the depletion rate is slow, the producing of calibration measurements and/or the performing of calibrations can be infrequent; if the depletion rate is faster, the frequency of producing of calibration measurements and/or the performing of calibrations can be increased.

A relatively sudden decrease in the magnitude of the calibration signal would indicate that the light source is on a non-linear portion of the depletion curve, possibly approaching the end of the light source's useful life. This information can be used to increase the frequency of producing calibration measurements and/or performing calibrations. Further, if a recalculated equation for the depletion curve is substantially the same as the previous equation, then it can be assumed that the light source is on the linear portion of the curve. However, if the recalculated equation is not substantially the same as the previous equation, then it can be assumed that the light source is on the non-linear portion of the depletion curve, and nearing the end of its useful life. Some or all of the above information, or other similar information, can be used to increase the frequency of producing calibration measurements and/or performing calibrations, and/or used to trigger an alert (detectable by a patient, clinician and/or physician) that indicates that one or more light source should be replaced.

Figure 13:
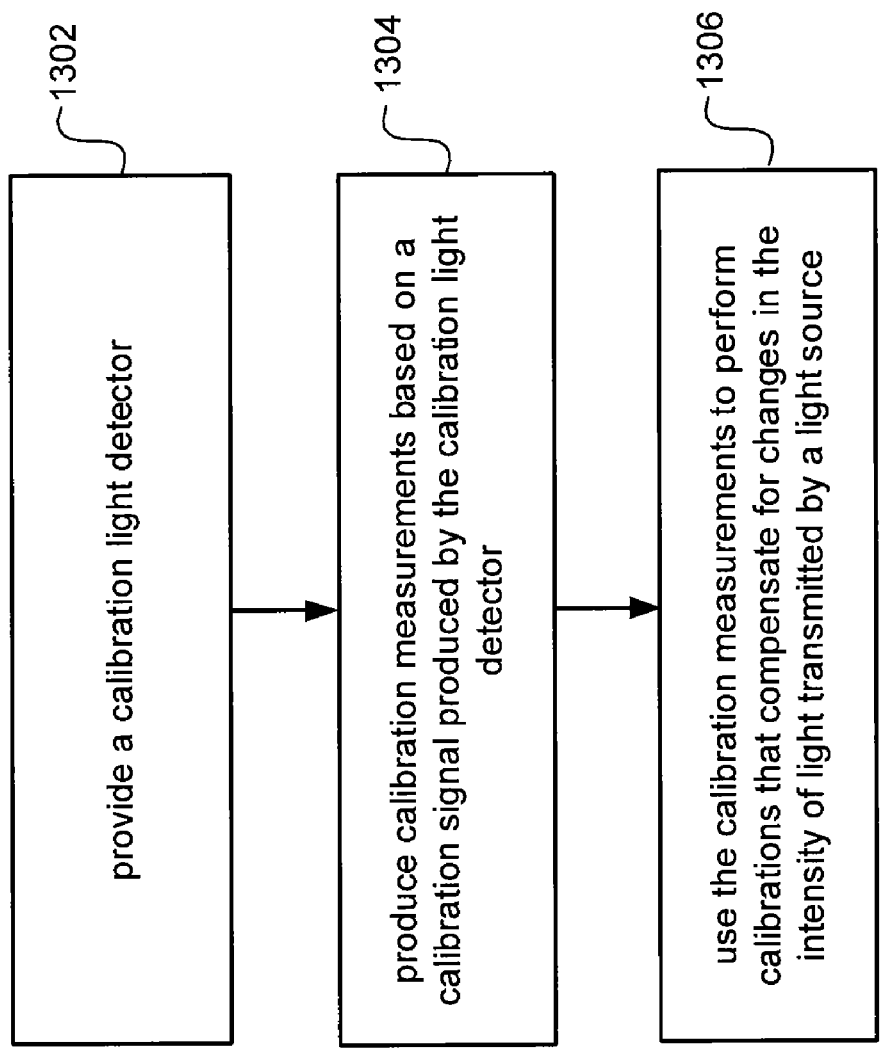
FIG. 13 is a high level flow diagram that is used to summarize various embodiments of the present invention that compensate for changes in intensity of light transmitted by a light source of an implantable system.

The various methods for compensating for changes in intensity of light transmitted by a light source of an implantable system will now be summarized with reference to FIG. 13. Such methods are especially useful with an implantable device that includes an implantable housing having a window through which light can pass, and a light source, within the housing, that transmits light, a portion of which exits the housing through the window. Such an implantable device also includes a measurement light detector, within the housing, to detect light scattered back into the housing through the window, and to produce a measurement signal that is indicative of the intensity of the light detected by the measurement light detector. Examples of such an implantable device were described above.

Referring to FIG. 13, as specified at step 1302, a calibration light detector is provided within the housing to detect a portion of the light that has not exited the housing, and to produce a calibration signal indicative of the intensity of the light detected by the calibration light detector, which is indicative of the intensity of the light transmitted by the light source. Referring to FIG. 11A, the calibration photo detector 1106 is an example of such a calibration light detector that is provided within the housing 804.

Referring again to FIG. 13, at step 1304, calibration measurements are produced based on the calibration signal. Step 1304 can include, as explained below, obtaining multiple samples or measurements of the calibration signal 1132, and integrating, averaging or otherwise combining such data to produce a single calibration measurement. Alternatively, a calibration measurement can be based on a single sample or measurement of the calibration signal 1132.

Referring again to FIG. 13, at step 1306, the calibration measurements are used to perform calibrations that compensate for changes in the intensity of light transmitted by the light source. Various ways that this can be accomplished in accordance with embodiment of the present invention were explained in detail above.

Depending on the exact implementation of the implantable device that includes a light source, movements by the patient that cause movements of the device, may or may not effect calibration measurements. In accordance with specific embodiments of the present invention, to minimize the chances of such movements affecting calibration measurements, and thus affecting the calibrations performed based on the calibration measurements, calibration measurements are only taken when the patient is at rest, or at least likely to be at rest. However, it is noted that this may not be necessary. Accordingly, in other embodiments, calibration measurements are taken without regard to whether the patient is at rest or not.

In certain embodiments, calibration measurements are only taken during times of the day when it is expected that the patient would be at rest, e.g., in the middle of the night when the patient is most likely sleeping. In accordance with other embodiments, one or more sensor (e.g., activity sensor) can be used to detect when a patient is at rest and/or supine, and calibrations measurements are only taken when the patient is sufficiently at rest, and/or supine. The following patents, which are each incorporated herein by reference, describe exemplary activity sensors that can be used: U.S. Pat. No. 6,658,292 to Kroll et al., entitled "Detection of Patient's Position and Activity Status using 3D Accelerometer-Based Position Sensor"; U.S. Pat. No. 6,466,821 to Kroll et al., entitled "Orientation of Patient's Position Sensor using External Field"; and U.S. Pat. No. 6,625,493 to Pianca et al., entitled "AC/DC Multi-Axis Accelerometer for Determining Patient Activity and Body Position." The use of other types of activity sensors are also within the scope of the present invention.

Instead of relying on an activity sensor to identify when calibrations measurements should be taken, other types of measures of physiological conditions may be used. For example, in a specific embodiment, calibrations measurements are only taken when the patient's heart rate is within a specified range or below a threshold. More generally, in certain embodiments, calibration measurements are only taken during consistent physiological conditions. In other embodiments, calibration measurements can be taken at any time, regardless of activity or other physiologic conditions of the patient.

In the above described embodiments, the calibration measurements were triggered by the implantable device, e.g., after a certain amount of time occurred since a last calibration measurement. In certain embodiments, even after the specified amount of time occurred since the last calibration measurement, the calibration measurement may not occur until the patient is determined to be at rest, or until other physiological conditions occur. It is also possible that calibration measurements are triggered telemetrically by an external device (e.g., device by 1502, shown in FIG. 15B).

As explained above, each time a calibration measurement is performed, to reduce effects of noise and potential erroneous signals, the calibration signal (and measurements thereof) produced for a light source can be integrated, averaged or otherwise combined over a specified period of time. For example, for a light source 102, a certain amount of calibration data can be collected starting at a time T1 and averaged to produce a calibration measurement $Cal_{T1}$. In other words, multiple samples or measurements of the calibration signal 1132 can be taken and averaged to produce a single calibration measurement that can be used to perform a calibration.

Where calibration data is not collected until the patient is at rest, following the start of a rest period, calibration data can be collected continuously or periodically for a preset or programmed period of time, or until the rest period ends. FIG. 14A illustrates an exemplary rest period. FIG. 14B illustrates that calibration data continually collected during the rest period, can be averaged or otherwise combined to produce a calibration measurement. FIG. 14C illustrates that calibration data periodically collected for shorter periods of time, can be averaged or otherwise combined to produce a calibration measurement. FIG. 14D illustrates that features (e.g., R-waves or P-waves) of an EGM can be used to trigger collection of calibration data. The collection of calibration data can begin when such a feature is detected, or a specified delay thereafter. A single data sample can be collected for each trigger, or data can be collected for a specified amount of time following each trigger.

Exemplary Stimulation Device

Figure 15A:
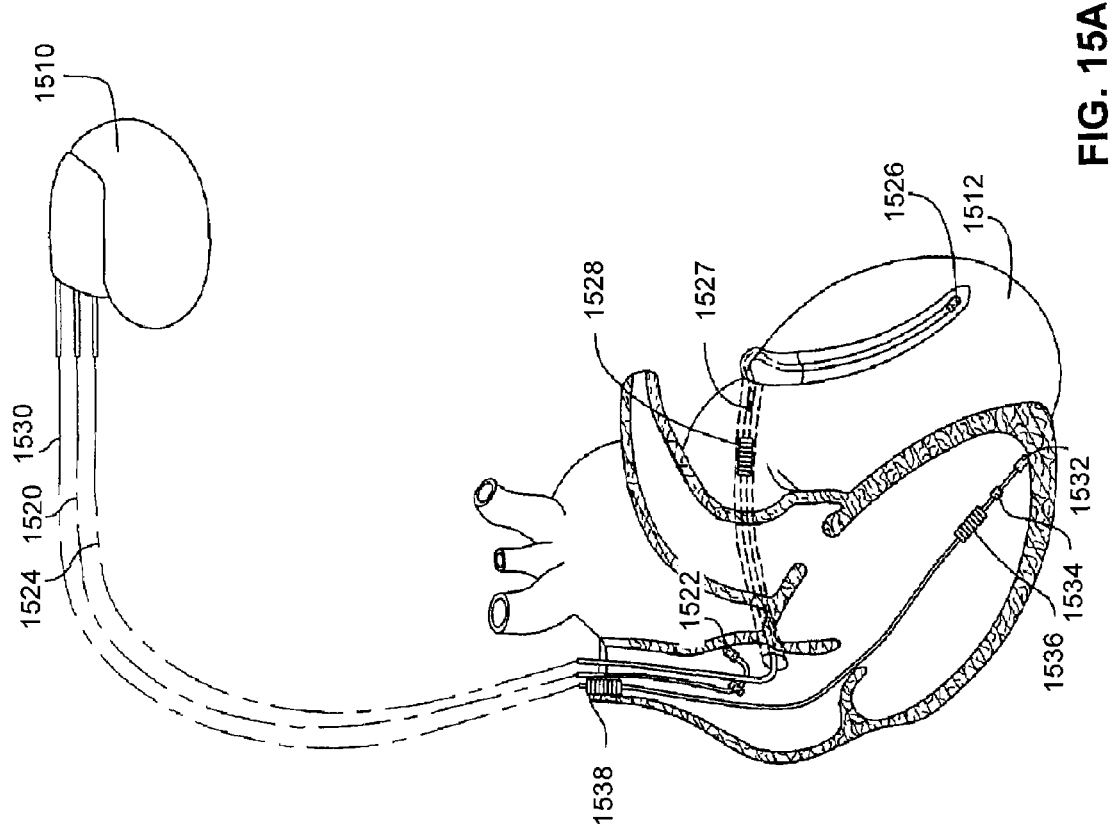
FIG. 15A illustrates an exemplary implantable stimulation device in electrical communication with a patient's heart by way of three leads, which are suitable for delivering multi-chamber stimulation and shock therapy.

Referring to FIG. 15A, the exemplary implantable stimulation device 1510 is shown as being in electrical communication with a patient's heart 1512 by way of three leads, 1520, 1524 and 1530, suitable for delivering multi-chamber stimulation and shock therapy. The sensor module 802 of the present invention can be placed within any of these leads, as was described above. Alternatively, a further dedicated lead or catheter can be provided for the purpose of containing the sensor 802 and placing the sensor 802 at a desired measurement site.

To sense atrial cardiac signals and to provide right atrial chamber stimulation therapy, the stimulation device 1510 is coupled to an implantable right atrial lead 1520 having at least an atrial tip electrode 1522, which typically is implanted in the patient's right atrial appendage.

To sense left atrial and ventricular cardiac signals and to provide left-chamber pacing therapy, the stimulation device 1510 is coupled to a "coronary sinus" lead 1524 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

The exemplary coronary sinus lead 1524 is designed to receive atrial and ventricular cardiac signals and to deliver left ventricular pacing therapy using at least a left ventricular tip electrode 1526, left atrial pacing therapy using at least a left atrial ring electrode 1527, and shocking therapy using at least a left atrial coil electrode 1528.

The stimulation device 1510 is also shown in electrical communication with the patient's heart 1515 by way of an implantable right ventricular lead 1530 having, in this embodiment, a right ventricular tip electrode 1532, a right ventricular ring electrode 1534, a right ventricular (RV) coil electrode 1536, and an SVC coil electrode 1538. Typically, the right ventricular lead 1530 is transvenously inserted into the heart 1512 so as to place the right ventricular tip electrode 1532 in the right ventricular apex so that the RV coil electrode 1536 will be positioned in the right ventricle and the SVC coil electrode 1538 will be positioned in the superior vena cava. Accordingly, the right ventricular lead 1530 is capable of receiving cardiac signals and delivering stimulation in the form of pacing and shock therapy to the right ventricle.

Figure 15B:
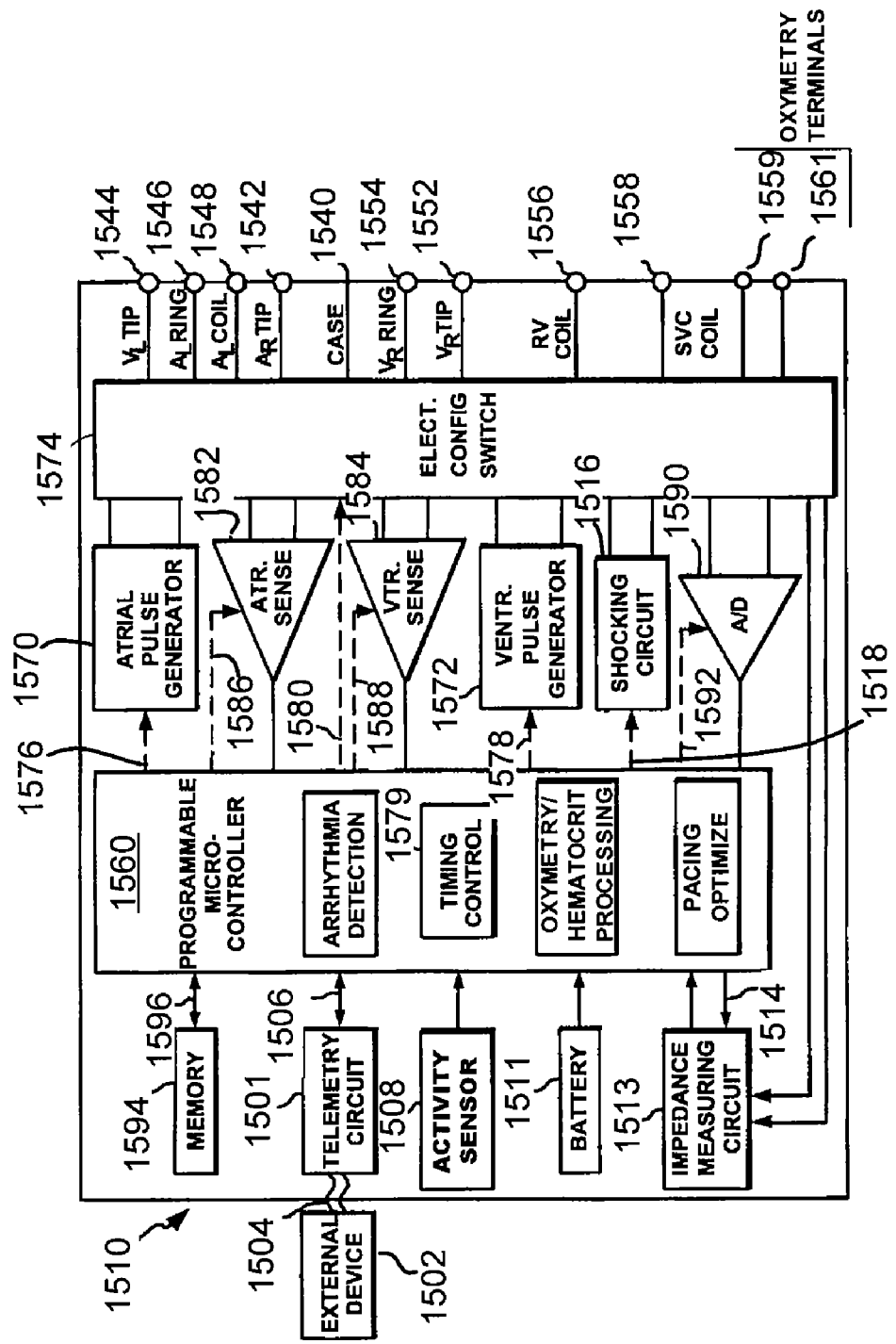
FIG. 15B is a simplified block diagram of the multi-chamber implantable stimulation device of FIG. 15A.

As illustrated in FIG. 15B, a simplified block diagram is shown of the multi-chamber implantable stimulation device 1510, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 1540 for the stimulation device 1510, shown schematically in FIG. 15B, is often referred to as the "can", "case" or "case electrode" and may be programmably selected to act as the return electrode for all "unipolar" modes. The housing 1540 may further be used as a return electrode alone or in combination with one or more of the coil electrodes, 1528, 1536 and 1538, for shocking purposes. The housing 1540 further includes a connector (not shown) having a plurality of terminals, 1542, 1544, 1546, 1548, 1552, 1554, 1556, and 1558 (shown schematically and, for convenience, the names of the electrodes to which they are connected are shown next to the terminals).

As such, to achieve right atrial sensing and pacing, the connector includes at least a right atrial tip terminal (AR TIP) 1542 adapted for connection to the atrial tip electrode 1522.

To achieve left chamber sensing, pacing and shocking, the connector includes at least a left ventricular tip terminal (VL TIP) 1544, a left atrial ring terminal (AL RING) 1546, and a left atrial shocking terminal (AL COIL) 1548, which are adapted for connection to the left ventricular tip electrode 1526, the left atrial ring electrode 1527, and the left atrial coil electrode 1528, respectively.

To support right chamber sensing, pacing and shocking, the connector further includes a right ventricular tip terminal (VR TIP) 1552, a right ventricular ring terminal (VR RING) 1554, a right ventricular shocking terminal (RV COIL) 1556, and an SVC shocking terminal (SVC COIL) 1558, which are adapted for connection to the right ventricular tip electrode 1532, right ventricular ring electrode 1534, the RV coil electrode 1536, and the SVC coil electrode 1538, respectively.

The connector is also shown as including terminals 1559 and 1561 (OXYMETRY TERMINALS), which are configured for connection to the wires 914 that are connected to the sensor module 802, to support the delivery of control signals to the sensor module 802, and to collect oxymetry data from the sensor module 802.

At the core of the stimulation device 1510 is a programmable microcontroller 1560 which controls the various modes of stimulation therapy, including pacing optimization and anti-arrhythmia therapy. The microcontroller 1560 can also determine measures of blood oxygen saturation and/or hematocrit based on the signals it receives from an oximetry sensor of the present invention. Such measures of oxygen saturation and/or hematocrit can be used, e.g., for pacing optimization, disease monitoring, and the like. Additionally or alternatively, the measures of oxygen saturation and/or hematocrit can be stored in memory 1594 for later transmission to an external device 1502 using the telemetry circuit 1501.

If the oxymetry sensor module 802 provides analog signals to the implantable device, then the terminals 1559 and 1561, through switch 1574, can provide such signals to an analog-to-digital (A/D) converter 1590 that converts the signals to a digital format understood by the microcontroller 1560. It is also possible that a dedicated A/D converter be provided within the implantable device 1510 for the purpose of digitizing signals received from the oximetry sensor. If the oxymetry sensor 802 provides digital signals to the implantable device 1510, then such signals may be provided directly to the microcontroller 1510, assuming it is the microcontroller 1560 that performs the processing that determines measures of blood oxygen saturation and/or hematocrit based on the signals. It is also possible that the implantable device 1510 include circuitry, external to the microcontroller 1560, which is dedicated to determining measures of blood oxygen saturation and/or hematocrit.

As is well known in the art, the microcontroller 1560 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 1560 includes the ability to analyze signals (data) as controlled by a program code stored in a designated block of memory. The details of the design of the microcontroller 1560 are not critical to the present invention. Rather, any suitable microcontroller 1560 can be used to carry out the functions described herein. The use of microprocessor-based control circuits for performing timing, control and data analysis functions are well known in the art.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the stimulation device and their inter-relationship, see U.S. Pat. No. 4,788,980 (Mann et. al.). The '052, '555, '298 and '980 patents are incorporated herein by reference.

As shown in FIG. 15B, an atrial pulse generator 1570 and a ventricular pulse generator 1572 generate pacing stimulation pulses for delivery by the right atrial lead 1520, the right ventricular lead 1530, and/or the coronary sinus lead 1524 via an electrode configuration switch 1574. It is understood that in order to provide stimulation therapy in each of the four chambers of the heart, the atrial and ventricular pulse generators, 1570 and 1572, may include dedicated, independent pulse generators, multiplexed pulse generators, or shared pulse generators. The pulse generators, 1570 and 1572, are controlled by the microcontroller 1560 via appropriate control signals, 1576 and 1578, respectively, to trigger or inhibit the stimulation pulses.

The microcontroller 1560 further includes timing control circuitry 1579 which is used to control pacing parameters (e.g., the timing of stimulation pulses) as well as to keep track of the timing of refractory periods, PVARP intervals, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 1574 includes a plurality of switches for connecting the desired electrodes to the appropriate I/O circuits, thereby providing complete electrode programmability. Accordingly, the switch 1574, in response to a control signal 1580 from the microcontroller 1560, determines the polarity of the stimulation pulses (e.g., unipolar, bipolar, combipolar, etc.) by selectively closing the appropriate combination of switches (not shown) as is known in the art. The switch 1574 can also be used to connect wires from an oximetry sensor 802 to appropriate I/O circuits.

Atrial sensing circuits 1582 and ventricular sensing circuits 1584 may also be selectively coupled to the right atrial lead 1520, coronary sinus lead 1524, and the right ventricular lead 1530, through the switch 1574 for detecting the presence of cardiac activity in each of the four chambers of the heart.

Accordingly, the atrial (ATR. SENSE) and ventricular (VTR. SENSE) sensing circuits, 1582 and 1584, may include dedicated sense amplifiers, multiplexed amplifiers, or shared amplifiers. The switch 1574 determines the "sensing polarity" of the cardiac signal by selectively closing the appropriate switches, as is also known in the art. In this way, the clinician may program the sensing polarity independent of the stimulation polarity.

Each sensing circuit, 1582 and 1584, preferably employs one or more low power, precision amplifiers with programmable gain and/or automatic gain control, bandpass filtering, and a threshold detection circuit, as known in the art, to selectively sense the cardiac signal of interest. The automatic gain control enables the device 1510 to deal effectively with the difficult problem of sensing the low amplitude signal characteristics of atrial or ventricular signals.

The outputs of the atrial and ventricular sensing circuits, 1582 and 1584, are connected to the microcontroller 1560 which, in turn, are able to trigger or inhibit the atrial and ventricular pulse generators, 1570 and 1572, respectively, in a demand fashion in response to the absence or presence of cardiac activity, in the appropriate chambers of the heart. The sensing circuits, 1582 and 1584, in turn, receive control signals over signal lines, 1586 and 1588, from the microcontroller 1560 for purposes of measuring cardiac performance at appropriate times, and for controlling the gain, threshold, polarization charge removal circuitry (not shown), and timing of any blocking circuitry (not shown) coupled to the inputs of the sensing circuits, 1582 and 1586.

For arrhythmia detection, the device 1510 utilizes the atrial and ventricular sensing circuits, 1582 and 1584, to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the microcontroller 1560 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 1590. The data acquisition system 1590 is configured to acquire intracardiac electrogram signals, convert the raw analog data into a digital signal, and store the digital signals for later processing and/or telemetric transmission to an external device 1502. The data acquisition system 1590 is coupled to the right atrial lead 1520, the coronary sinus lead 1524, and the right ventricular lead 1530 through the switch 1574 to sample cardiac signals across any pair of desired electrodes.

Advantageously, the data acquisition system 1590 can be coupled to the microcontroller 1560, or other detection circuitry, for detecting an evoked response from the heart 1515 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 1560 detects a depolarization signal during a window following a stimulation pulse, the presence of which indicates that capture has occurred. The microcontroller 1560 enables capture detection by triggering the ventricular pulse generator 1572 to generate a stimulation pulse, starting a capture detection window using the timing control circuitry 1579 within the microcontroller 1560, and enabling the data acquisition system 1590 via control signal 1592 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 1560 is further coupled to a memory 1594 by a suitable data/address bus 1596, wherein the programmable operating parameters used by the microcontroller 1560 are stored and modified, as required, in order to customize the operation of the stimulation device 1510 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 1515 within each respective tier of therapy.

Data acquired by the data acquisition system 1590 (and optionally stored) can be used for subsequent analysis to guide the programming of the device and/or to monitor oxygen saturation and/or hematocrit, appropriately adjust pacing interval parameters, select optimum pacing intervals, and/or select appropriate anti-arrhythmia therapy.

Advantageously, the operating parameters of the implantable device 1510 may be non-invasively programmed into the memory 1594 through a telemetry circuit 1501 in telemetric communication with the external device 1502, such as a programmer, transtelephonic transceiver, or a diagnostic system analyzer. The telemetry circuit 1501 is activated by the microcontroller by a control signal 1506. The telemetry circuit 1501 advantageously allows intracardiac electrograms, oxygen saturation information, hematocrit information and status information relating to the operation of the device 1510 (as contained in the microcontroller 1560 or memory 1594) to be sent to an external device 1502 through an established communication link 1504.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient Generation of Sensing Signals in an Implantable Medical Device such as a Pacemaker or ICD" (note: this relates to transfer of EGM data) (McClure et al.), which patents are hereby incorporated herein by reference.

The stimulation device 1510 can further include one or more activity and/or physiologic sensor 1508, which can be located within the stimulation device housing 1540 as shown, or can be located external to the housing. Exemplary activity sensors were mentioned above.

The stimulation device 1510 additionally includes a battery 1515 which provides operating power to all of the circuits shown in FIG. 15B. For the stimulation device 1510, which employs shocking therapy, the battery 1515 must be capable of operating at low current drains for long periods of time, and then be capable of providing high-current pulses (for capacitor charging) when the patient requires a shock pulse. The battery 1515 should also have a predictable discharge characteristic so that elective replacement time can be detected. Accordingly, the device 1510 preferably employs lithium/silver vanadium oxide batteries, but is not limited thereto.

The stimulation device 1510 can further include a magnet detection circuitry (not shown), coupled to the microcontroller 1560. It is the purpose of the magnet detection circuitry to detect when a magnet is placed over the stimulation device 1510, which magnet may be used by a clinician to perform various test functions of the stimulation device 1510 and/or to signal the microcontroller 1560 that the external programmer 1502 is in place to receive or transmit data to the microcontroller 1560 through the telemetry circuits 1501.

As further shown in FIG. 15B, the device 1510 is shown as having an impedance measuring circuit 1513 which is enabled by the microcontroller 1560 via a control signal 1514. The known uses for an impedance measuring circuit 1513 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; measuring thoracic impedance for detecting and assessing the severity of pulmonary edema; detecting when the device has been implanted; measuring stroke volume; and detecting the opening of heart valves, etc. The impedance measuring circuit 1513 is advantageously coupled to the switch 1574 so that any desired electrode may be used. In addition, to facilitate the measurement of peripheral tissue edema, extra electrodes can be added to the device housing, thereby limiting the test electric field to the peripheral tissue.

In the case where the stimulation device 1510 is also intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 1560 further controls a shocking circuit 1516 by way of a control signal 1518. The shocking circuit 1516 generates shocking pulses of low (up to 0.5 Joules), moderate (0.5-10 Joules), or high energy (12 to 40 Joules), as controlled by the microcontroller 1560. Such shocking pulses are applied to the patient's heart 1512 through at least two shocking electrodes, and as shown in this embodiment, selected from the left atrial coil electrode 1528, the RV coil electrode 1536, and/or the SVC coil electrode 1538. As noted above, the housing 1540 may act as an active electrode in combination with the RV electrode 1536, or as part of a split electrical vector using the SVC coil electrode 1538 or the left atrial coil electrode 1528 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized to be recognize), and pertaining exclusively to the treatment of ventricular fibrillation. Accordingly, the microcontroller 1260 is capable of controlling the synchronous or asynchronous delivery of the shocking pulses. Another approach to electrical anti-arrhythmia therapy is anti-tachycardia pacing, in which low-voltage pacing pulses are applied to pace-terminate the arrhythmia. This approach is particularly effective in low rate ventricular tachycardias.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for compensating for changes in intensity of light transmitted by a light source of an implantable system that includes
    an implantable housing including a window through which light can pass;
    a light source, within the housing, that transmits light, wherein a portion of the light exits the housing through the window; and
    a measurement light detector, within the housing, to detect light scattered back into the housing through the window, and to produce a measurement signal that is indicative of the intensity of the light detected by the measurement light detector;
the method comprising:
(a) providing a calibration light detector within the housing to detect a portion of the light that has not exited the housing, and to produce a calibration signal indicative of the intensity of the light detected by the calibration light detector, which is indicative of the intensity of the light transmitted by the light source;
(b) producing calibration measurements based on the calibration signal;
(c) using the calibration measurements to perform calibrations that compensate for changes in the intensity of light transmitted by the light source; and
(d) between consecutive calibration measurements, predicting a metric indicative of a change in the intensity of the light since a most recent calibration measurement, and using the predicted metric to perform a calibration that compensates for predicted depletion in the intensity of light transmitted by the light source.

2. The method of claim 1, wherein step (c) includes:
    detecting changes in the intensity of the light transmitted by the light source based on the calibration measurements; and
    taking into account the detected changes in the intensity of the transmitted light when using the measurement signal for a diagnostic and/or therapeutic purpose.

3. The method of claim 2, further comprising using the measurement signal to determine levels of blood oxygen saturation and/or levels of hematocrit, wherein the detected changes in the intensity of the transmitted light are taken into account when using the measurement signal to determine levels of blood oxygen saturation and/or levels of hematocrit.

4. The method of claim 1, wherein step (c) includes:
    adjusting the measurement signal, based on the calibration measurements, to compensate for changes in the intensity of the light transmitted by the light source.

5. The method of claim 1, wherein step (c) includes:
    adjusting a drive signal that drives the light source, based on the calibration measurements, to keep the intensity of the light transmitted by the light source substantially constant.

6. The method of claim 1, wherein calibrations performed at step (c) are performed periodically.

7. The method of claim 1, wherein calibrations measurements produced at step (b) are produced periodically.

8. The method of claim 7, wherein:
    calibrations performed at step (c) are performed periodically;
    calibrations measurements produced at step (b) are produced periodically; and
    calibrations are performed at step (c) more often than calibration measurements are produced at step (b).

9. The method of claim 1, wherein calibration measurements are only taken at step (b) when it is determined or presumed that the patient is at rest.

10. The method of claim 1, wherein step (b) includes using the calibration light detector to obtain calibration data for a period of time, and averaging or otherwise combining the calibration data to produce a said calibration measurement.

11. A method for compensating for changes in intensity of light transmitted by a light source of an implantable system that includes
- an implantable housing including a window through which light can pass;
- a light source, within the housing, that transmits light, wherein a portion of the light exits the housing through the window; and
- a measurement light detector, within the housing, to detect light scattered back into the housing through the window, and to produce a measurement signal that is indicative of the intensity of the light detected by the measurement light detector;

the method comprising:
(a) providing a calibration light detector within the housing to detect a portion of the light that has not exited the housing, and to produce a calibration signal indicative of the intensity of the light detected by the calibration light detector, which is indicative of the intensity of the light transmitted by the light source;
(b) producing calibration measurements based on the calibration signal;
(c) using the calibration measurements to perform calibrations that compensate for changes in the intensity of light transmitted by the light source;
(d) estimating a depletion curve for the light source based on calibration measurements; and
(e) between consecutive calibration measurements, using the estimated depletion curve to perform a calibration that compensates for predicted depletion in the intensity of light transmitted by the light source.

12. A method for compensating for changes in intensity of light transmitted by a light source of an implantable system that includes
- an implantable housing including a window through which light can pass;
- a light source, within the housing, that transmits light, wherein a portion of the light exits the housing through the window; and
- a measurement light detector, within the housing, to detect light scattered back into the housing through the window, and to produce a measurement signal that is indicative of the intensity of the light detected by the measurement light detector;

the method comprising:
(a) providing a calibration light detector within the housing to detect a portion of the light that has not exited the housing, and to produce a calibration signal indicative of the intensity of the light detected by the calibration light detector, which is indicative of the intensity of the light transmitted by the light source;
(b) producing calibration measurements based on the calibration signal; and
(c) using the calibration measurements to perform calibrations that compensate for changes in the intensity of light transmitted by the light source, wherein:
- calibrations measurements produced at step (b) are produced periodically;
- the implantable system includes multiple said light sources, each of which transmits light of a corresponding wavelength;
- the measurement light detector detects light from each said light source scattered back into the housing through the window, and produces a said measurement signal for each said light source;
- the calibration light detector produced calibration measurements for each said light source at step (b); and
- calibrations are separately performed for each said light source at step (c).

13. The method of claim 12, wherein calibrations are performed at step (c) more often than calibration measurements are produced at step (b).

14. An implantable system, comprising:
- an implantable housing including a window through which light can pass;
- a light source, within the housing, that transmits light, wherein a portion of the light exits the housing through the window;
- a measurement light detector, within the housing, to detect light scattered back into the housing through the window, and to produce a measurement signal that is indicative of the intensity of the light detected by the measurement light detector;
- a calibration light detector within the housing to detect a portion of the light that has not exited the housing, and to produce calibration measurements based on the calibration signal, the calibration measurements indicative of the intensity of the light detected by the calibration light detector, which are indicative of the intensity of the light transmitted by the light source; and
- a processor to use the calibration measurements to perform calibrations that compensate for changes in the intensity of light transmitted by the light source, wherein the processor, between consecutive calibration measurements, predicts a metric indicative of a change in the intensity of the light since a most recent calibration measurement, and uses the predicted metric to perform a calibration that compensates for predicted depletion in the intensity of light transmitted by the light source.

15. An implantable system, comprising:
- an implantable housing including a window through which light can pass;
- a light source, within the housing, that transmits light, wherein a portion of the light exits the housing through the window;
- a measurement light detector, within the housing, to detect light scattered back into the housing through the window, and to produce a measurement signal that is indicative of the intensity of the light detected by the measurement light detector;
- a calibration light detector within the housing to detect a portion of the light that has not exited the housing, and to produce calibration measurements based on the calibration signal, the calibration measurements indicative of the intensity of the light detected by the calibration light detector, which are indicative of the intensity of the light transmitted by the light source; and
- a processor to use the calibration measurements to perform calibrations that compensate for changes in the intensity of light transmitted by the light source, wherein the processor, between consecutive calibration measurements, uses a depletion curve for the light source to perform a calibration that compensates for predicted depletion in the intensity of light transmitted by the light source.

16. The system of claim 15, wherein the processor estimates the depletion curve for the light source based on calibration measurements.

17. The system of claim 15, wherein the depletion curve is provided by a manufacturer of the light source.

* * * * *